(12) United States Patent
Luttrull et al.

(10) Patent No.: US 10,285,859 B2
(45) Date of Patent: *May 14, 2019

(54) SYSTEM FOR PERFORMING RETINA PHOTOSTIMULATION

(71) Applicant: Ojai Retinal Technology, LLC, Ojai, CA (US)

(72) Inventors: Jeffrey K. Luttrull, Ojai, CA (US); Benjamin W. L. Margolis, Oakland, CA (US); David B. Chang, Tustin, CA (US)

(73) Assignee: Ojai Retinal Technology, LLC, Ojai, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/291,796

(22) Filed: Oct. 12, 2016

(65) Prior Publication Data
US 2017/0027755 A1  Feb. 2, 2017

Related U.S. Application Data

(60) Division of application No. 15/148,842, filed on May 6, 2016, which is a continuation-in-part of application
(Continued)

(51) Int. Cl.
*A61B 18/20* (2006.01)
*A61F 9/008* (2006.01)
(Continued)

(52) U.S. Cl.
CPC ...... *A61F 9/00823* (2013.01); *A61F 9/00817* (2013.01); *A61F 9/00821* (2013.01);
(Continued)

(58) Field of Classification Search
CPC .......... A61N 5/0613; A61N 5/04; A61N 1/40; A61N 2/002; A61N 2/006; A61N 5/0618;
(Continued)

(56) References Cited

U.S. PATENT DOCUMENTS 3,408,593 A  10/1968  Hurtwitz, Jr.
4,048,011 A  9/1977  Kovin et al.
(Continued)

FOREIGN PATENT DOCUMENTS

WO  2006005038 A2  1/2006
WO  2007035855 A2  3/2007
(Continued)

OTHER PUBLICATIONS

Sramek et al. (Non-damaging Retinal Phototherapy: Dynamic Range of Heat Shock Protein Expression, Mar. 2011, Investigative Ophthalmology and Visual Science, vol. 52, No. 3, pp. 1780-1787) (Year: 2011).*
(Continued)

*Primary Examiner* — Aaron F Roane
(74) *Attorney, Agent, or Firm* — Kelly & Kelley, LLP

(57) ABSTRACT

A process for performing retinal phototherapy or photostimulation includes generating a laser light that creates a therapeutic effect to retinal and/or foveal tissues exposed to the laser light without destroying or permanently damaging the retinal or foveal tissue. The laser light is applied to a first treatment area of the retina. After a predetermined interval of time, within a single treatment session, the laser light is reapplied to the first treatment area of the retina. During the interval of time between the laser light applications to the first treatment area, the laser light is applied to one or more additional areas of the retina that is spaced apart from the first treatment area and one another. The laser light is repeatedly applied to each of the areas to be treated until a predetermined number of laser light applications to each area to be treated has been achieved.

33 Claims, 16 Drawing Sheets

Related U.S. Application Data

No. 14/921,890, filed on Oct. 23, 2015, now Pat. No. 9,381,116, which is a continuation-in-part of application No. 14/607,959, filed on Jan. 28, 2015, now Pat. No. 9,168,174, which is a continuation-in-part of application No. 13/798,523, filed on Mar. 13, 2013, now Pat. No. 10,219,947, which is a continuation-in-part of application No. 13/481,124, filed on May 25, 2012, now Pat. No. 9,381,115, application No. 15/291,796, filed on Oct. 12, 2016, which is a continuation-in-part of application No. 15/075,432, filed on Mar. 21, 2016, which is a continuation of application No. 13/798,523, filed on Mar. 13, 2013, now Pat. No. 10,219,947, which is a continuation-in-part of application No. 13/481,124, filed on May 25, 2012, now Pat. No. 9,381,115.

(51) Int. Cl.
    *A61N 5/06* (2006.01)
    *A61N 5/067* (2006.01)
    *A61B 90/00* (2016.01)

(52) U.S. Cl.
    CPC .......... *A61N 5/0613* (2013.01); *A61B 90/361* (2016.02); *A61F 9/008* (2013.01); *A61F 2009/00863* (2013.01); *A61F 2009/00897* (2013.01); *A61N 2005/067* (2013.01)

(58) Field of Classification Search
    CPC ...... A61N 2005/007; A61N 2005/0602; A61N 2005/0647; A61N 2005/0652; A61N 2005/0654; A61N 2005/0659; A61N 2005/0662; A61N 2005/067; A61N 2007/0078; A61N 2007/0095; A61F 2007/0002
    USPC .......................................................... 607/88
    See application file for complete search history.

(56) References Cited

U.S. PATENT DOCUMENTS

| | | | |
|---|---|---|---|
| 4,176,325 A | 11/1979 | Kajimura et al. | |
| 4,194,114 A | 3/1980 | Pankratov et al. | |
| 4,410,365 A | 10/1983 | Glukhovsky et al. | |
| 4,695,733 A | 9/1987 | Pesavento | |
| 4,730,335 A | 3/1988 | Clark et al. | |
| 4,791,634 A | 12/1988 | Miyake | |
| 4,865,029 A | 9/1989 | Pankratov et al. | |
| 4,879,722 A | 11/1989 | Dixon et al. | |
| 4,930,504 A | 6/1990 | Diamantopoulos et al. | |
| 4,933,944 A | 6/1990 | McGraw | |
| 4,935,931 A | 6/1990 | McGraw | |
| 4,961,079 A | 10/1990 | Owens et al. | |
| 4,967,416 A | 10/1990 | Esterowitz et al. | |
| 5,037,421 A | 8/1991 | Boutacoff et al. | |
| 5,067,951 A | 11/1991 | Greve | |
| 5,085,492 A | 2/1992 | Kelsoe et al. | |
| 5,088,803 A | 2/1992 | Buzawa | |
| 5,147,354 A | 9/1992 | Boutacoff et al. | |
| 5,152,759 A * | 10/1992 | Parel | A61F 9/008 606/17 |
| 5,372,595 A | 12/1994 | Gaasterland et al. | |
| 5,394,199 A | 2/1995 | Flower | |
| 5,430,756 A | 7/1995 | Hanihara | |
| 5,520,680 A | 5/1996 | Shapshay et al. | |
| 5,651,019 A | 7/1997 | Goldberg et al. | |
| 5,982,789 A | 11/1999 | Marshall et al. | |
| 6,050,990 A | 4/2000 | Tankovich et al. | |
| 6,066,128 A | 5/2000 | Bahmanyar et al. | |
| 6,186,628 B1 * | 2/2001 | Van de Velde | A61F 9/008 351/205 |
| 6,208,769 B1 | 3/2001 | Pankratov | |
| 6,222,869 B1 | 4/2001 | Marshall et al. | |
| 6,327,291 B1 | 12/2001 | Marshall | |
| 6,377,599 B1 | 4/2002 | Marshall | |
| 6,540,391 B2 | 4/2003 | Lanzeffa et al. | |
| 6,681,185 B1 | 1/2004 | Young et al. | |
| 6,715,877 B2 | 4/2004 | Molebny | |
| 6,733,490 B1 | 5/2004 | Falsini et al. | |
| 6,813,942 B1 | 11/2004 | Vozhdaev et al. | |
| 6,889,695 B2 | 5/2005 | Pankratov et al. | |
| 6,942,655 B2 | 9/2005 | Peyman | |
| 7,227,196 B2 | 6/2007 | Burgener, II et al. | |
| 7,229,435 B2 | 6/2007 | Nakamura | |
| 7,387,785 B1 | 6/2008 | Rudin et al. | |
| 7,452,081 B2 | 11/2008 | Wiltberger et al. | |
| 7,645,276 B2 | 1/2010 | Pankratov et al. | |
| 7,763,828 B2 | 7/2010 | Talwar et al. | |
| 7,766,903 B2 | 8/2010 | Blumenkranz et al. | |
| 7,766,904 B2 | 8/2010 | McGowan, Sr. et al. | |
| 7,771,417 B2 | 8/2010 | Telfair et al. | |
| 7,909,816 B2 | 3/2011 | Buzawa | |
| 8,454,161 B2 | 6/2013 | Su et al. | |
| 9,192,780 B2 | 11/2015 | McDaniel | |
| 2002/0099363 A1 | 7/2002 | Woodward et al. | |
| 2002/0120255 A1 | 8/2002 | Sotiropoulos et al. | |
| 2002/0165525 A1 | 11/2002 | Nakamura | |
| 2003/0009155 A1 * | 1/2003 | Pawlowski | A61F 9/008 606/4 |
| 2003/0179344 A1 | 9/2003 | Van de Velde | |
| 2004/0098074 A1 | 5/2004 | Mohr et al. | |
| 2005/0069531 A1 | 3/2005 | Karageozian et al. | |
| 2005/0176662 A1 | 8/2005 | Inana et al. | |
| 2007/0173793 A1 | 7/2007 | Rathjen | |
| 2007/0213693 A1 | 9/2007 | Plunkett | |
| 2008/0015553 A1 | 1/2008 | Zacharias | |
| 2010/0049180 A1 | 2/2010 | Wells et al. | |
| 2010/0152716 A1 | 6/2010 | Previn et al. | |
| 2010/0168724 A1 | 7/2010 | Sramek et al. | |
| 2010/0249760 A1 | 9/2010 | Blumenkranz et al. | |
| 2010/0290007 A1 | 11/2010 | Van de Velde | |
| 2011/0098692 A1 | 4/2011 | Shazly et al. | |
| 2011/0196350 A1 | 8/2011 | Friedman et al. | |
| 2013/0116672 A1 | 5/2013 | Yee | |
| 2013/0317570 A1 | 11/2013 | Luttrull et al. | |
| 2014/0324031 A1 * | 10/2014 | Abe | A61F 9/008 606/4 |

FOREIGN PATENT DOCUMENTS

| | | | |
|---|---|---|---|
| WO | WO 2007035855 A2 * | 3/2007 | A61B 18/22 |
| WO | 2007106521 A2 | 9/2007 | |

OTHER PUBLICATIONS

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Luttrull, J K et al.; Subthreshold diode micropulse photocoagulation for the treatment of clinically significant diabetic macular oedema; Eye (2009) Macmillan Publishers Limited 2009.

Luttrull et al. Subthreshold diode micropulse panretinal photocoagulation for proliferative diabetic retinopathy. Eye (2007), 1-6 © 2007 Nature Publishing Group, www.nature.com/eye.

Small Beam Diameter Scanning Galvo Mirror Systems; Thorlabs; 1999-2013, 4 pgs.

(56) References Cited

OTHER PUBLICATIONS

Keller, Matthew D. et al.; Raman Spectroscopy for Cancer Diagnosis; www.spectroscopyonline.com; Nov. 21, 2006 (11); pp. 33-41 (including Reference (21) thereof).
International Search Report for PCT/US2015/0060836 dated Jan. 29, 2016.
Sramek, et al., Non-Damaging Retinal Phototherapy: Dynamic Range of Heat Shock Protein Expression; Investigative Ophthalmology & Visual Science, Mar. 2011, vol. 52, No. 3, pp. 1780-1787.

\* cited by examiner

SYSTEM FOR PERFORMING RETINA PHOTOSTIMULATION

RELATED APPLICATIONS

This application is a divisional of U.S. Ser. No. 15/148,842, filed May 6, 2016, which is a continuation-in-part of U.S. application Ser. No. 14/921,890, filed Oct. 23, 2015, which is a continuation-in-part of U.S. application Ser. No. 14/607,959, filed Jan. 28, 2015 (now U.S. Pat. No. 9,168,174), which is a continuation-in-part of U.S. application Ser. No. 13/798,523, filed Mar. 13, 2013, which is a continuation-in-part of U.S. application Ser. No. 13/481,124, filed May 25, 2012; and is also a continuation-in-part of U.S. application Ser. No. 15/075,432, filed Mar. 21, 2016, which is a continuation of U.S. application Ser. No. 13/798,523, filed Mar. 13, 2013, which is a continuation-in-part of U.S. application Ser. No. 13/481,124, filed May 25, 2012.

BACKGROUND OF THE INVENTION

The present invention generally relates to phototherapy or photostimulation of biological tissue, such as laser retinal photocoagulation therapy. More particularly, the present invention is directed to a system and process for treating retinal diseases and disorders by using harmless, subthreshold phototherapy or photostimulation of the retina.

Complications of diabetic retinopathy remain a leading cause of vision loss in people under sixty years of age. Diabetic macular edema is the most common cause of legal blindness in this patient group. Diabetes mellitus, the cause of diabetic retinopathy, and thus diabetic macular edema, is increasing in incidence and prevalence worldwide, becoming epidemic not only in the developed world, but in the developing world as well. Diabetic retinopathy may begin to appear in persons with Type I (insulin-dependent) diabetes within three to five years of disease onset. The prevalence of diabetic retinopathy increases with duration of disease. By ten years, 14%-25% of patients will have diabetic macular edema. By twenty years, nearly 100% will have some degree of diabetic retinopathy. Untreated, patients with clinically significant diabetic macular edema have a 32% three-year risk of potentially disabling moderate visual loss.

Until the advent of thermal retinal photocoagulation, there was generally no effective treatment for diabetic retinopathy. Using photocoagulation to produce photothermal retinal burns as a therapeutic maneuver was prompted by the observation that the complications of diabetic retinopathy were often less severe in eyes with preexisting retinal scarring from other causes. The Early Treatment of Diabetic Retinopathy Study demonstrated the efficacy of argon laser macular photocoagulation in the treatment of diabetic macular edema. Full-thickness retinal laser burns in the areas of retinal pathology were created, visible at the time of treatment as white or gray retinal lesions ("suprathreshold" retinal photocoagulation). With time, these lesions developed into focal areas of chorioretinal scarring and progressive atrophy.

With visible endpoint photocoagulation, laser light absorption heats pigmented tissues at the laser site. Heat conduction spreads this temperature increase from the retinal pigment epithelium and choroid to overlying non-pigmented and adjacent unexposed tissues. Laser lesions become visible immediately when damaged neural retina overlying the laser sight loses its transparency and scatters white ophthalmoscopic light back towards the observer.

There are different exposure thresholds for retinal lesions that are haemorrhagic, ophthalmoscopically apparent, or angiographically demonstrable. A "threshold" lesion is one that is barely visible ophthalmoscopically at treatment time, a "subthreshold" lesion is one that is not visible at treatment time, and "suprathreshold" laser therapy is retinal photocoagulation performed to a readily visible endpoint. Traditional retinal photocoagulation treatment requires a visible endpoint either to produce a "threshold" lesion or a "suprathreshold" lesion so as to be readily visible and tracked. In fact, it has been believed that actual tissue damage and scarring are necessary in order to create the benefits of the procedure. The gray to white retinal burns testify to the thermal retinal destruction inherent in conventional threshold and suprathreshold photocoagulation. Photocoagulation has been found to be an effective means of producing retinal scars, and has become the technical standard for macular photocoagulation for diabetic macular edema for nearly 50 years.

With reference now to FIG. 1, a diagrammatic view of an eye, generally referred to by the reference number 10, is shown. When using phototherapy, the laser light is passed through the patient's cornea 12, pupil 14, and lens 16 and directed onto the retina 18. The retina 18 is a thin tissue layer which captures light and transforms it into the electrical signals for the brain. It has many blood vessels, such as those referred to by reference number 20, to nourish it. Various retinal diseases and disorders, and particularly vascular retinal diseases such as diabetic retinopathy, are treated using conventional thermal retinal photocoagulation, as discussed above. The fovea/macula region, referred to by the reference number 22 in FIG. 1, is a portion of the eye used for color vision and fine detail vision. The fovea is at the center of the macula, where the concentration of the cells needed for central vision is the highest. Although it is this area where diseases such as age-related macular degeneration are so damaging, this is the area where conventional photocoagulation phototherapy cannot be used as damaging the cells in the foveal area can significantly damage the patient's vision. Thus, with current convention photocoagulation therapies, the foveal region is avoided.

That iatrogenic retinal damage is necessary for effective laser treatment of retinal vascular disease has been universally accepted for almost five decades, and remains the prevailing notion. Although providing a clear advantage compared to no treatment, current retinal photocoagulation treatments, which produce visible gray to white retinal burns and scarring, have disadvantages and drawbacks. Conventional photocoagulation is often painful. Local anesthesia, with its own attendant risks, may be required. Alternatively, treatment may be divided into stages over an extended period of time to minimize treatment pain and post-operative inflammation. Transient reduction in visual acuity is common following conventional photocoagulation.

In fact, thermal tissue damage may be the sole source of the many potential complications of conventional photocoagulation which may lead to immediate and late visual loss. Such complications include inadvertent foveal burns, pre- and sub-retinal fibrosis, choroidal neovascularization, and progressive expansion of laser scars. Inflammation resulting from the tissue destruction may cause or exacerbate macular edema, induced precipitous contraction of fibrovascular proliferation with retinal detachment and vitreous hemorrhage, and cause uveitis, serous choroidal detachment, angle closure or hypotony. Some of these complications are rare, while others, including treatment pain, progressive scar expansion, visual field loss, transient visual loss and decreased night vision are so common as to be accepted as inevitable side-effects of conventional laser retinal photocoagulation. In fact, due to the retinal damage inherent in conventional photocoagulation treatment, it has been limited in density and in proximity to the fovea, where the most visually disabling diabetic macular edema occurs.

Notwithstanding the risks and drawbacks, retinal photocoagulation treatment, typically using a visible laser light, is the current standard of care for proliferative diabetic retinopathy, as well as other retinopathy and retinal diseases, including diabetic macular edema and retinal venous occlusive diseases which also respond well to retinal photocoagulation treatment. In fact, retinal photocoagulation is the current standard of care for many retinal diseases, including diabetic retinopathy.

Another problem is that the treatment requires the application of a large number of laser doses to the retina, which can be tedious and time-consuming. Typically, such treatments call for the application of each dose in the form of a laser beam spot applied to the target tissue for a predetermined amount of time, from a few hundred milliseconds to several seconds. Typically, the laser spots range from 50-500 microns in diameter. Their laser wavelength may be green, yellow, red or even infrared. It is not uncommon for hundreds or even in excess of one thousand laser spots to be necessary in order to fully treat the retina. The physician is responsible for insuring that each laser beam spot is properly positioned away from sensitive areas of the eye, such as the fovea, that could result in permanent damage. Laying down a uniform pattern is difficult and the pattern is typically more random than geometric in distribution. Point-by-point treatment of a large number of locations tends to be a lengthy procedure, which frequently results in physician fatigue and patient discomfort.

U.S. Pat. No. 6,066,128, to Bahmanyar describes a method of multi-spot laser application, in the form of retinal-destructive laser photocoagulation, achieved by means of distribution of laser irradiation through an array of multiple separate fiber optic channels and micro lenses. While overcoming the disadvantages of a point-by-point laser spot procedure, this method also has drawbacks. A limitation of the Bahmanyar method is differential degradation or breakage of the fiber optics or losses due to splitting the laser source into multiple fibers, which can lead to uneven, inefficient and/or suboptimal energy application. Another limitation is the constraint on the size and density of the individual laser spots inherent in the use of an optical system of light transmission fibers in micro lens systems. The mechanical constraint of dealing with fiber bundles can also lead to limitations and difficulties focusing and aiming the multi-spot array.

U.S. Patent Publication 2010/0152716 A1 to Previn describes a different system to apply destructive laser irradiation to the retina using a large retinal laser spot with a speckle pattern, oscillated at a high frequency to homogenize the laser irradiance throughout the spot. However, a problem with this method is the uneven heat buildup, with higher tissue temperatures likely to occur toward the center of the large spot. This is aggravated by uneven heat dissipation by the ocular circulation resulting in more efficient cooling towards the margins of the large spot compared to the center. That is, the speckle pattern being oscillated at a high frequency can cause the laser spots to be overlapping or so close to one another that heat builds up and undesirable tissue damage occurs. Previn's speckle technique achieves averaging of point laser exposure within the larger exposure via the random fluctuations of the speckle pattern. However, such averaging results from some point exposures being more intense than others, whereas some areas within the exposure area may end with insufficient laser exposure, whereas other areas will receive excessive laser exposure. In fact, Previn specifically notes the risk of excessive exposure or exposure of sensitive areas, such as the fovea, which should be avoided with this system. Although these excessively exposed spots may result in retinal damage, Previn's invention is explicitly intended to apply damaging retinal photocoagulation to the retina, other than the sensitive area such as the fovea.

All conventional retinal photocoagulation treatments, including those described by Previn and Bahmanyar, create visible endpoint laser photocoagulation in the form of gray to white retinal burns and lesions, as discussed above. Accordingly, there is a continuing need for a system and method for retina phototherapy which does not create detectable retinal burns and lesions and thus does not permanently damage or destroy the retinal tissue. There is also a continuing need for such a system and method which can be applied to the entire retina, including sensitive areas such as the fovea, without visible tissue damage or the resulting drawbacks or complications of conventional visible retinal photocoagulation treatments. There is an additional need for such a system and method for treating the entire retina, or at least a portion of the retina, in a less laborious and time-consuming manner. The present invention fulfills these needs, and provides other related advantages.

SUMMARY OF THE INVENTION

Recently, the inventor has discovered that subthreshold photocoagulation in which no visible tissue damage or laser lesions were detectable by any known means including ophthalmoscopy; infrared, color, red-free or autofluorescence fundus photography in standard or retro-mode; intravenous fundus fluorescein or indocyanine green angiographically, or Spectral-domain optical coherence tomography at the time of treatment or any time thereafter has produced similar beneficial results and treatment without many of the drawbacks and complications resulting from conventional visible threshold and suprathreshold photocoagulation treatments. It has been determined that with the proper operating parameters, subthreshold photocoagulation treatment can be, and may ideally be, applied to the entire retina, including sensitive areas such as the fovea, without visible tissue damage or the resulting drawbacks or complications of conventional visible retinal photocoagulation treatments. In fact, studies published by the inventor reveal that treatment is not only harmless, it uniquely improves function of the retina and fovea in a wide variety of retinopathies immediately and is thus restorative to the retina (Luttrull J K, Margolis B W L. Functionally guided retinal protective therapy as prophylaxis for age-related and inherited retinal degenerations. A pilot study. Invest Ophthalmol Vis Sci. 2016 Jan. 1; 5 7(1):265-75.). Moreover, by desiring to treat the entire retina, or confluently treat portions of the retina, laborious and time-consuming point-by-point laser spot therapy can be avoided. In addition, the inefficiencies and inaccuracies inherent to invisible endpoint laser treatment resulting in suboptimal tissue target coverage can also be avoided.

The present invention resides in a process and system for treating retinal diseases and disorders by means of harmless, restorative subthreshold photocoagulation phototherapy. Although the present invention is particularly useful in treating diabetic retinopathy, including diabetic macular edema, it will be understood that the present invention also applies to all other retinal conditions, including but not limited to retinal venous occlusive diseases and idiopathic central serous chorioretinopathy, proliferative diabetic retinopathy, and retinal macroaneurysm as reported, which respond well to traditional retinal photocoagulation treatments; but having potential application as preventative and rejuvenative in disorders such as genetic diseases and age-related macular degeneration and others; and as neuroprotective treatment in glaucoma.

In accordance with the present invention, a system for performing retinal phototherapy or photostimulation comprises a laser console generating a micropulsed laser light beam. The laser light beam is passed through an optical lens or mask to optically shape the laser light beam. A coaxial wide-field non-contact digital optical viewing camera projects the laser light beam to an area of a desired site for performing retinal phototherapy or photostimulation. A mechanism controllably moves the laser light beam during micropulse intervals to at least one other area of the desired site for performing retinal phototherapy or photostimulation, and subsequently returns the laser light beam to a previously treated area within a predetermined period of time during the same treatment session to reapply the laser light beam to that area.

The laser light beam typically has a wavelength greater than 532 nm. The laser light radiant beam may have an infrared wavelength such as between 750 nm-1300 nm, and preferably approximately 810 nm. The laser has a duty cycle of less than 10%, and typically a duty cycle of 5% or less. The exposure envelope of the laser is generally 500 milliseconds or less, and the micropulse frequency is preferably 500 Hz. The light beam may have an intensity between 100-590 watts per square centimeter, and preferably approximately 350 watts per square centimeter. The laser console may generate a plurality of micropulsed light beams, at least a plurality of the light beams having different waves.

The optical lens or mask may optically shape the light beam from the laser console into a geometric object or pattern. This may be done by diffractive optics to simultaneously generate a plurality of therapeutic beams or spots from the laser light beam, wherein the plurality of spots are projected from the coaxial wide-field non-contact digital optical viewing camera to at least a portion of the desired site for performing retinal phototherapy or photostimulation.

The laser light beam is controllably moved, such as using an optical scanning mechanism, to achieve complete coverage of the desired site for performing retinal phototherapy or photostimulation. The laser light beam may be selectively applied to disease markers on the desired site for performing retinal phototherapy or photostimulation. The laser light beam may be projected to at least a portion of the center of the desired site for performing retinal phototherapy or photostimulation. A fundus image of the desired site for performing retinal phototherapy or photostimulation may be displayed parallel to or super imposed over a result image from a retinal diagnostic modality.

The laser light beam or geometric object or pattern is incrementally moved a sufficient distance from where the light beam was previously applied to the retina, to avoid tissue damage, prior to reapplying the light beam to the retina. The laser light beam is controllably returned to the previously treated area within less than a second from the previous application of the laser light to the area. More typically, the laser light beam is returned to the previously treated area within one millisecond to three milliseconds.

In accordance with the present invention, a process for performing retinal phototherapy or photostimulation comprises the step of generating a laser light that creates a therapeutic effect to retinal and/or foveal tissue exposed to the laser light without destroying or permanently damaging the retinal or foveal tissue. Parameters of the generated laser light beam, including the pulse length, power, and duty cycle are selected to create a therapeutic effect with no visible laser lesions or tissue damage detected ophthalmoscopically or angiographically or to any currently known means after treatment.

The laser light is applied to a first treatment area of the retina and/or fovea. The entire retina, including the fovea, may be treated without damaging retinal or foveal tissue while still providing the benefits of photocoagulation treatment in accordance with the present invention.

After a predetermined interval of time, within a single treatment session, the laser light is reapplied to the first treatment area of the retina and/or fovea. During the interval of time between the laser light applications to the first treatment area, the laser light is applied to at least a second treatment area of the retina and/or fovea that is spaced apart from the first treatment area. During the same treatment session, the laser light is repeatedly applied to each of the areas to be treated until a predetermined number of laser light applications to each area to be treated has been achieved. The predetermined number of laser light applications to each treatment area is 50 to 200, and more typically 75 to 150.

The laser light is reapplied to a treatment area within a predetermined interval of time from the immediately prior laser light application to that area. The interval of time between laser light applications to a treatment area is less than one second, and typically between one millisecond and three milliseconds. During the interval of time between laser light treatment applications to a treatment area, laser light is moved and is applied to other treatment areas of the retina and/or fovea. Typically, the laser light is reapplied to previously treated areas in sequence.

The laser light application comprises a single micropulse of laser light, which pulse is less than a millisecond in duration, and may be between 50 microseconds to 100 microseconds in duration. During the remainder of the predetermined interval, laser light treatment applications are applied to other treatment areas of the retina. This may include at least a portion of the fovea. The laser light may be applied to the entire retina and fovea. This would be done by controllably moving the laser light spots to create treatment areas of the retina. The adjacent areas are separated by at least a predetermined minimum distance to avoid thermal tissue damage. Any and all areas of the retina can be treated in accordance with the present invention as true subthreshold photocoagulation is achieved in which no visible tissue damage or laser lesions are detected by any known means, yet a therapeutic effect is provided to the retinal tissue.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The present invention relates to a system and process for treating retinal diseases, including vascular retinal diseases such as diabetic retinopathy and diabetic macular edema, by means of predetermined parameters producing harmless, true subthreshold photocoagulation. The inventor's finding that retinal laser treatment that does not cause any laser-induced retinal damage, but can be at least as effective as conventional retinal photocoagulation is contrary to conventional thinking and practice.

Conventional thinking assumes that the physician must intentionally create retinal damage as a prerequisite to therapeutically effective treatment. With reference to FIG. 2, FIGS. 2A-2D are graphic representations of the effective surface area of various modes of retinal laser treatment for retinal vascular disease. The gray background represents the retina 18 which is unaffected by the laser treatment. The black areas 24 are areas of the retina which are destroyed by conventional laser techniques. The lighter gray or white areas 26 represent the areas of the retina secondarily affected by the laser, but not destroyed.

Figure 1:
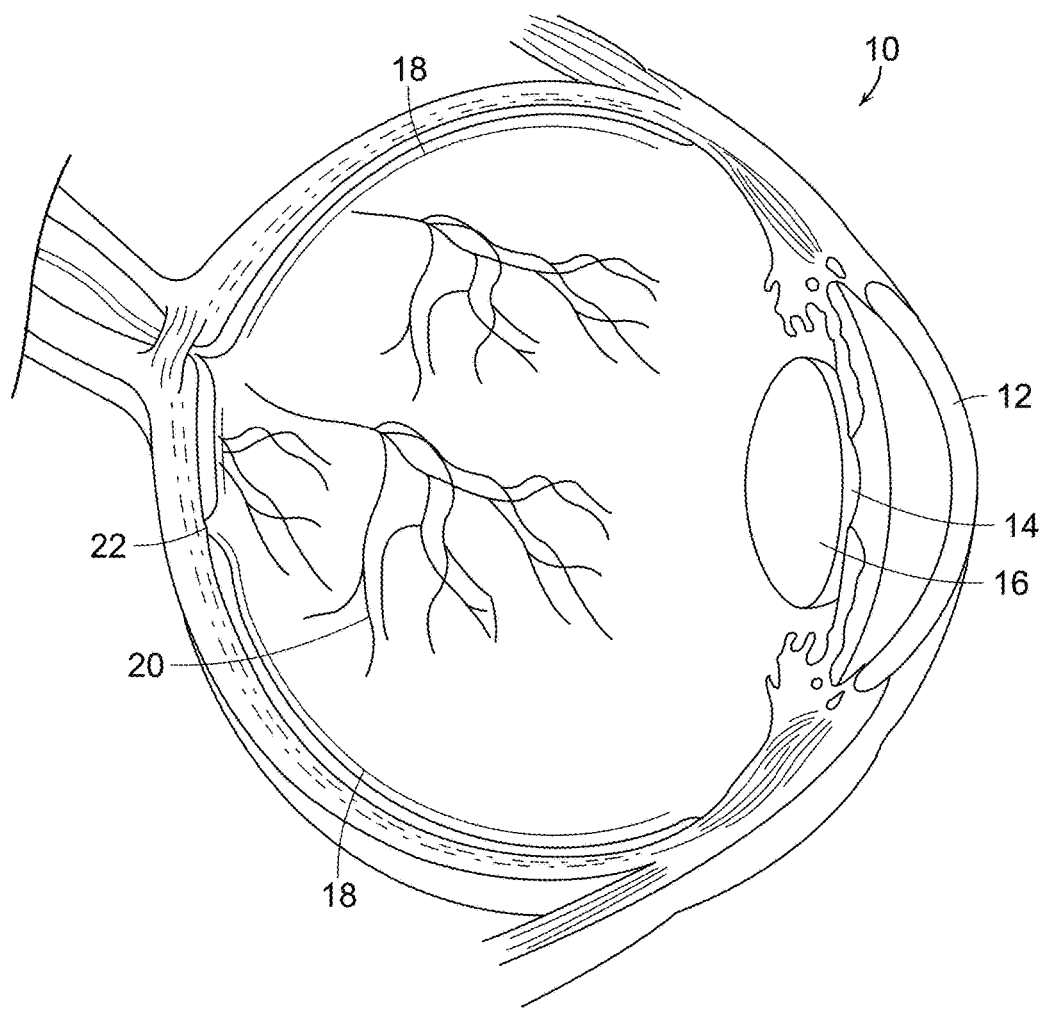
FIG. 1 is a cross-sectional diagrammatic view of a human eye.
Figure 2A:
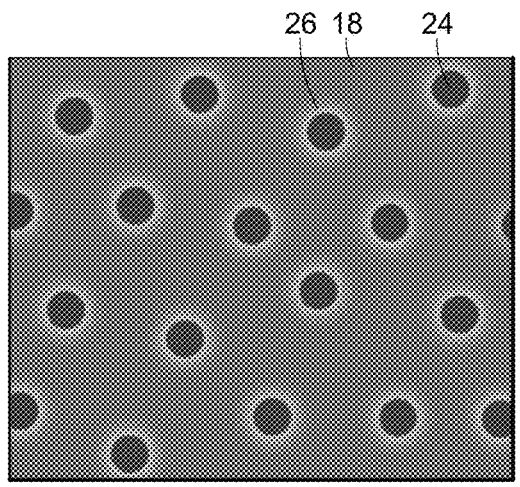
FIGS. 2A-2D are graphic representations of the effective surface area of various modes of retinal laser treatment in accordance with the prior art.

FIG. 2A illustrates the therapeutic effect of conventional argon laser retinal photocoagulation. The therapeutic effects attributed to laser-induced thermal retinal destruction include reduced metabolic demand, debulking of diseased retina, increased intraocular oxygen tension and ultra production of vasoactive cytokines, including vascular endothelial growth factor (VEGF).

Figure 2B:
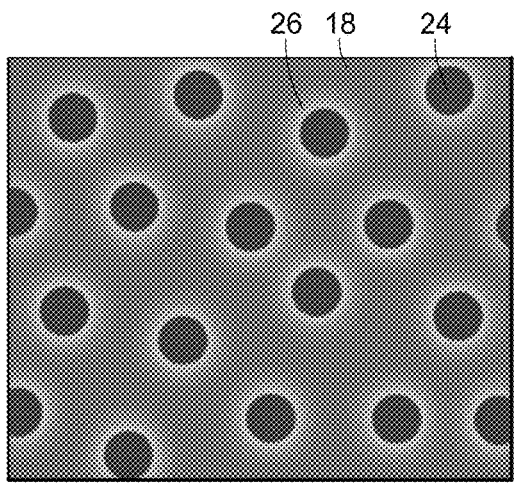
Figure 2C:
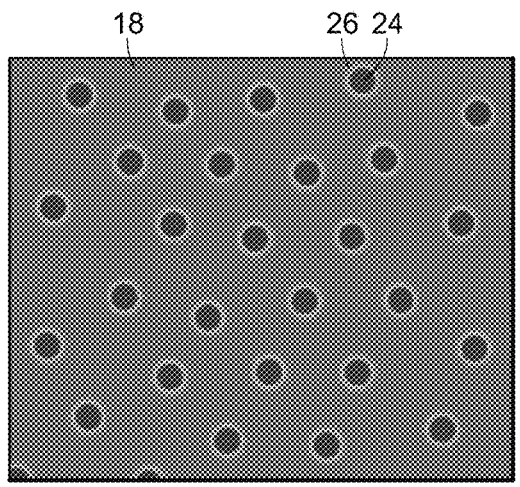

With reference to FIG. 2B, increasing the burn intensity of the traditional laser burn is shown. It will be seen that the burned and damaged tissue area 24 is larger, which has resulted in a larger "halo effect" of heated, but undamaged, surrounding tissue 26. Laboratory studies have shown that increased burn intensity is associated with an enhanced therapeutic effect, but hampered by increased loss of functional retina and inflammation. However, with reference to FIG. 2C, when the intensity of the conventional argon laser photocoagulation is reduced, the area of the retina 26 affected by the laser but not destroyed is also reduced, which may explain the inferior clinical results from lower-intensity/lower-density or "mild" argon laser grid photocoagulation compared to higher-intensity/higher-density treatment, as illustrated in FIG. 2B.

Figure 2D:
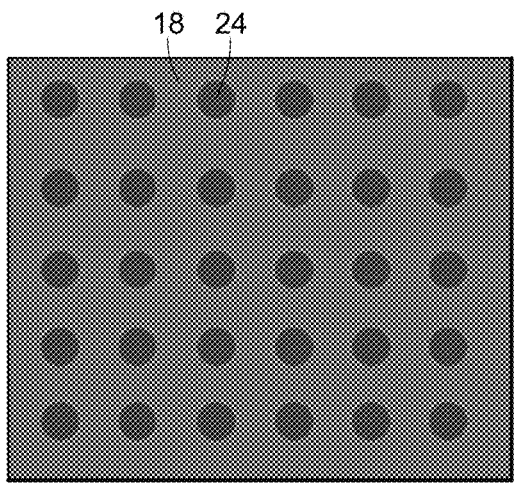

With reference to FIG. 2D, it has been found that low-fluence photocoagulation with short-pulse continuous wave laser photocoagulation, also known as selective retinal therapy, produces minimal optical and lateral spread of laser photothermal tissue effects, to the extent that the area of the retina affected by the laser but not destroyed is minimal to nonexistent. Thus, despite damage or complete ablation of the directly treated retina 18, the rim of the therapeutically affected and surviving tissue is scant or absent. This explains the recent reports finding superiority of conventional argon laser photocoagulation over PASCAL for diabetic retinopathy.

However, the inventor has shown that such thermal retinal damage is unnecessary and questioned whether it accounts for the benefits of the conventional laser treatments. Instead, the inventor has surmised that the therapeutic alterations in the retinal pigment epithelium (RPE) cytokine production elicited by conventional photocoagulation comes from cells at the margins of traditional laser burns, affected but not killed by the laser exposure, referred to by the reference number 26 in FIG. 2.

Figure 3A:
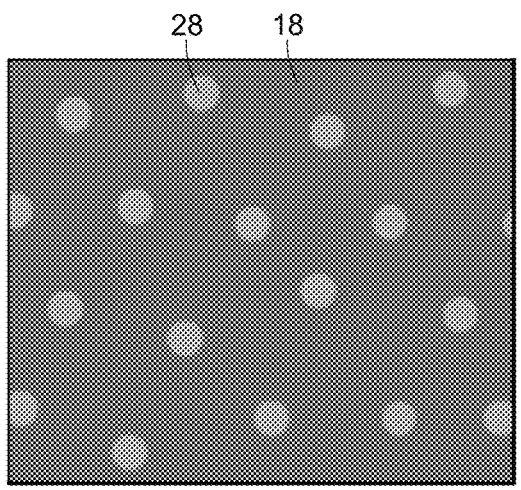
FIGS. 3A and 3B are graphic representations of effective surface areas of retinal laser treatment, in accordance with the present invention.

FIG. 3A represents the use of a low-intensity and low-density laser, such as a micropulsed diode laser in accordance with the invention, sometimes referred to herein as subthreshold diode micropulse laser treatment (SDM). This creates "true" subthreshold or invisible retinal photocoagulation, shown graphically for exemplary purposes by the reference number 28, without any visible burn areas 32. All areas of the retinal pigment epithelium 18 exposed to the laser irradiation are preserved, and available to contribute therapeutically.

The subthreshold retinal photocoagulation, sometimes referred to as "true subthreshold", of the invention is defined as retinal laser applications biomicroscopically invisible at the time of treatment. Unfortunately, the term "subthreshold" has often been used in the art to describe several different clinical scenarios reflecting widely varying degrees of laser-induced thermal retinal damage. The use of the term "subthreshold" falls into three categories reflecting common usage and the historical and morphological evolution of reduced-intensity photocoagulation for retinal vascular disease toward truly invisible phototherapy or true subthreshold photocoagulation which the invention embodies.

"Classical subthreshold" for photocoagulation describes the early attempts at laser intensity reduction using conventional continuous argon, krypton, and diode lasers. Although the retinal burns were notably less obvious than the conventional "threshold" (photocoagulation confined to the outer retina and thus less visible at time of treatment) or even milder "suprathreshold" (full-thickness retinal photocoagulation generally easily visible at the time of treatment), the lesions of "classical" subthreshold photocoagulation were uniformly visible both clinically and by fundus fluorescein angiography (FFA) at the time of treatment and thereafter.

"Clinical subthreshold" photocoagulation describes the next epiphany of evolution of laser-induced retinal damage reduction, describing a lower-intensity but persistently damaging retinal photocoagulation using either a micropulsed laser or short-pulsed continuous wave laser that better confine the damage to the outer retina and retinal pigmentation epithelium. In "clinical" subthreshold photocoagulation, the laser lesions may in fact be ophthalmoscopically invisible at the time of treatment, however, as laser-induced retinal damage remains the intended point of treatment, laser lesions are produced which generally become increasingly clinically visible with time, and many, if not all, laser lesions can be seen by FFA, fundus autofluorescence photography (FAF), and/or spectral-domain (SD) optical coherence tomography (OCT) at the time of treatment and thereafter.

Figure 3B:
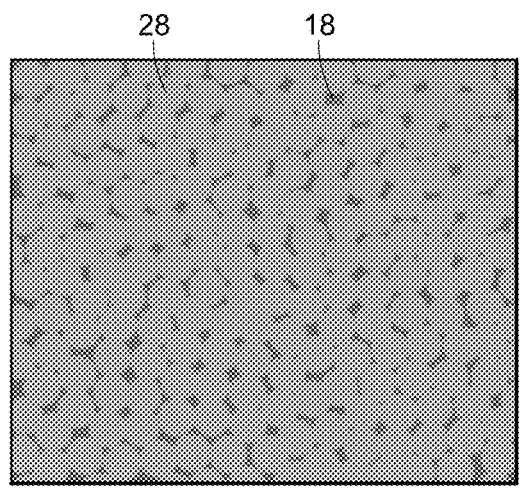

"True" subthreshold photocoagulation, as a result of the present invention, is invisible and includes laser treatment non-discernible by any other known means such as FFA, FAF, or even SD-OCT. "True subthreshold" photocoagulation is therefore defined as a laser treatment which produces absolutely no retinal damage detectable by any means at the time of treatment or any time thereafter by known means of detection. As such, with the absence of lesions and other tissue damage and destruction, FIGS. 3A and 3B diagrammatically represent the result of "true", invisible subthreshold photocoagulation.

Various parameters have been determined to achieve "true" subthreshold or "low-intensity" effective photocoagulation. These include providing sufficient power to produce effective treatment retinal laser exposure, but not too high to create tissue damage or destruction. True subthreshold laser applications can be applied singly or to create a geometric object or pattern of any size and configuration to minimize heat accumulation, but assure uniform heat distribution as well as maximizing heat dissipation such as by using a low duty cycle. The inventor has discovered how to achieve therapeutically effective and harmless true subthreshold retinal laser treatment. The inventor has also discovered that placement of true subthreshold laser applications confluently and contiguously to the retinal surface improves and maximizes the therapeutic benefits of treatment without harm or retinal damage.

The American Standards Institute (ANSI) has developed standards for safe workplace laser exposure based on the combination of theoretical and empirical data. The "maximum permissible exposure" (MPE) is the safety level, set at approximately $1/10^{th}$ of the laser exposure level expected to produce biological effects. At a laser exposure level of 1 times MPE, absolute safety would be expected and retinal exposure to laser radiation at this level would be expected to have no biologic affect. Based on ANSI data, a 50% of some risk of suffering a barely visible (threshold) retinal burn is generally encountered at 10 times MPE for conventional continuous wave laser exposure. For a low-duty cycle micropulsed laser exposure of the same power, the risk of threshold retinal burn is approximately 100 times MPE. Thus, the therapeutic range—the interval of doing nothing at all and the 50% of some likelihood of producing a threshold retinal burn—for low-duty cycle micropulsed laser irradiation is 10 times wider than for continuous wave laser irradiation with the same energy. It has been determined that safe and effective subthreshold photocoagulation using a low-duty cycle micropulsed diode laser is between 18 times and 55 times MPE, such as with a preferred laser exposure to the retina at 47 times MPE for a near-infrared 810 nm diode laser. At this level, the inventor has observed that there is therapeutic effectiveness with no retinal damage whatsoever.

It has been found that the intensity or power of a low-duty cycle 810 nm laser beam between 100 watts to 590 watts per square centimeter is effective yet safe. A particularly preferred intensity or power of the laser light beam is approximately 250-350 watts per square centimeter for an 810 nm micropulsed diode laser.

Power limitations in current micropulsed diode lasers require fairly long exposure duration. The longer the laser exposure, the more important the center-spot heat dissipating ability toward the unexposed tissue at the margins of the laser spot and toward the underlying choriocapillaris. Thus, the radiant beam of an 810 nm diode laser should have an exposure envelope duration of 500 milliseconds or less, and preferably approximately 100-300 milliseconds. Of course, if micropulsed diode lasers become more powerful, the exposure duration will be lessened accordingly. It will be understood that the exposure envelope duration is a duration of time where the micropulsed laser beam would be exposed to the same spot or location of the retina, although the actual time of exposure of the tissue to the laser is much less as the laser light pulse is less than a millisecond in duration, and typically between 50 microseconds to 100 microseconds in duration.

Invisible phototherapy or true subthreshold photocoagulation in accordance with the present invention can be performed at various laser light wavelengths, such as from a range of 532 nm to 1300 nm. Use of a different wavelength can impact the preferred intensity or power of the laser light beam and the exposure envelope duration in order that the retinal tissue is not damaged, yet therapeutic effect is achieved.

Another parameter of the present invention is the duty cycle (the frequency of the train of micropulses, or the length of the thermal relaxation time in between consecutive pulses). It has been found that the use of a 10% duty cycle or higher adjusted to deliver micropulsed laser at similar irradiance at similar MPE levels significantly increase the risk of lethal cell injury, particularly in darker fundi. However, duty cycles less than 10%, and preferably approximately 5% duty cycle or less demonstrated adequate thermal rise and treatment at the level of the RPE cell to stimulate a biologic response, but remained below the level expected to produce lethal cell injury, even in darkly pigmented fundi. Moreover, if the duty cycle is less than 5%, the exposure envelope duration in some instances can exceed 500 milliseconds.

In a particularly preferred embodiment, the use of small retinal laser spots is used. This is due to the fact that larger spots can contribute to uneven heat distribution and insufficient heat dissipation within the large retinal laser spot, potentially causing tissue damage or even tissue destruction towards the center of the larger laser spot. In this usage, "small" would generally apply to retinal spots less than 3 mm in diameter. However, the smaller the retinal spot, the more ideal the heat dissipation and uniform energy application becomes. Thus, at the power intensity and exposure duration described above, small spots, such as 25-300 micrometers in diameter, or small geometric lines or other objects are preferred so as to maximize even heat distribution and heat dissipation to avoid tissue damage.

Thus, the following key parameters have been found in order to create harmless, "true" subthreshold photocoagulation in accordance with the present invention: a) a low (preferably 5% or less) duty cycle; b) a small spot size to minimize heat accumulation and assure uniform heat distribution within a given laser spot so as to maximize heat dissipation; c) sufficient power to produce retinal laser exposures of between 18 times-55 times MPE producing an RPE temperature rise of 7° C.-14° C.; and retinal irradiance of between 100-590 W/cm².

Using the foregoing parameters, a harmless yet therapeutically effective "true" subthreshold or invisible photocoagulation phototherapy treatment can be attained which has been found to produce the benefits of conventional photocoagulation phototherapy, but avoid the drawbacks and complications of conventional phototherapy. In fact, "true" subthreshold photocoagulation phototherapy in accordance with the present invention enables the physician to apply a "low-intensity/high-density" phototherapy treatment, such as illustrated in FIG. 3B, and treat the entire retina, including sensitive areas such as the macula and even the fovea without creating visual loss or other damage. As indicated above, using conventional phototherapies, the entire retina, and particularly the fovea, cannot be treated as it will create vision loss due to the tissue damage in sensitive areas.

Conventional retina-damaging laser treatment is limited in treatment density, requiring subtotal treatment of the retina, including subtotal treatment of the particular areas of retinal abnormality. However, recent studies demonstrate that eyes in diabetics may have diffuse retinal abnormalities without otherwise clinically visible diabetic retinopathy, and eyes with localized areas of clinically identifiable abnormality, such as diabetic macular edema or central serous chorioretinopathy, often have total retinal dysfunction detectable only by retinal function testing. The ability of the invention to harmlessly treat the entire retina thus allows, for the first time, both preventative and therapeutic treatment of eyes with retinal disease completely rather than locally or subtotally; and early treatment prior to the manifestation of clinical retinal disease and visual loss.

As discussed above, it is conventional thinking that tissue damage and lesions must be created in order to have a therapeutic effect. However, the inventor has found that this simply is not the case. In the absence of laser-induced retinal damage, there is no loss of functional retinal tissue and no inflammatory response to treatment. Adverse treatment effects are thus completely eliminated and functional retina preserved rather than sacrificed. This may yield superior visual acuity results compared to conventional photocoagulation treatment.

The present invention spares the neurosensory retina and is selectively absorbed by the RPE. Current theories of the pathogenesis of retinal vascular disease especially implicate cytokines, potent extra cellular vasoactive factors produced by the RPE, as important mediators of retinal vascular disease. The present invention both selectively targets and avoids lethal buildup within RPE. Thus, with the present invention the capacity for the treated RPE to participate in a therapeutic response is preserved and even enhanced rather than eliminated as a result their destruction of the RPE in conventional photocoagulation therapies.

It has been noted that the clinical effects of cytokines may follow a "U-shaped curve" where small physiologic changes in cytokine production, denoted by the left side of curve, may have large clinical effects comparable to high-dose (pharmacologic) therapy (denoted by the right side of the curve). Using sublethal laser exposures in accordance with the present invention may be working on the left side of the curve where the treatment response may approximate more of an "on/off" phenomenon rather than a dose-response. This might explain the clinical effectiveness of the present invention observed at low reported irradiances. This is also consistent with clinical experience and in-vitro studies of laser-tissue interaction, wherein increasing irradiance may simply increase the risk of thermal retinal damage without improving the therapeutic effect.

Another mechanism through which SDM might work is the activation of heat shock proteins (HSPs). Despite a near infinite variety of possible cellular abnormalities, cells of all types share a common and highly conserved mechanism of repair: heat shock proteins (HSPs). HSPs are elicited almost immediately, in seconds to minutes, by almost any type of cell stress or injury. In the absence of lethal cell injury, HSPs are extremely effective at repairing and returning the viable cell toward a more normal functional state. Although HSPs are transient, generally peaking in hours and persisting for a few days, their effects may be long lasting. HSPs reduce inflammation, a common factor in many retinal disorders, including diabetic retinopathy (DR) and AMD.

Laser treatment induces HSP activation and, in the case of retinal treatment, thus alters and normalizes retinal cytokine expression. The more sudden and severe the non-lethal cellular stress (such as laser irradiation), the more rapid and robust HSP production. Thus, a burst of repetitive low temperature thermal spikes at a very steep rate of change (~20° C. elevation with each 100 μs micropulse, or 20,000° C./sec) produced by each SDM exposure is especially effective in stimulating production of HSPs, particularly compared to non-lethal exposure to subthreshold treatment with continuous wave lasers, which can duplicate only the low average tissue temperature rise.

Laser wavelengths below 532 nm produce increasingly cytotoxic photochemical effects. At 532 nm-1300 nm, SDM produces photothermal, rather than photochemical, cellular stress. Thus, SDM is able to affect the tissue, including RPE, without damaging it. Consistent with HSP activation, SDM produces prompt clinical effects, such as rapid and significant improvement in retinal electrophysiology, visual acuity, contrast visual acuity and improved macular sensitivity measured by microperimetry, as well as long-term effects, such as reduction of DME and involution of retinal neovascularization.

In the retina, the clinical benefits of SDM are thus produced by sub-morbid photothermal RPE HSP activation. In dysfunctional RPE cells, HSP stimulation by SDM results in normalized cytokine expression, and consequently improved retinal structure and function. The therapeutic effects of this "low-intensity" laser/tissue interaction are then amplified by "high-density" laser application, recruiting all the dysfunctional RPE in the targeted area, thereby maximizing the treatment effect. These principles define the treatment strategy of SDM described herein. The ability of SDM to produce therapeutic effects similar to both drugs and photocoagulation indicates that laser-induced retinal damage (for effects other than cautery) is unnecessary and non-therapeutic; and, in fact, detrimental because of the loss of retinal function and incitement of inflammation.

Because normally functioning cells are not in need of repair, HSP stimulation in normal cells would tend to have no notable clinical effect. The "patho-selectivity" of near infrared laser effects, such as SDM, affecting sick cells but not affecting normal ones, on various cell types is consistent with clinical observations of SDM. This facility is key to the suitability of SDM for early and preventative treatment of eyes with chronic progressive disease and eyes with minimal retinal abnormality and minimal dysfunction. Finally, SDM has been reported to have a clinically broad therapeutic range, unique among retinal laser modalities, consistent with American National Standards Institute "Maximum Permissible Exposure" predictions. While SDM may cause direct photothermal effects such as entropic protein unfolding and disaggregation, SDM appears optimized for clinically safe and effective stimulation of HSP-mediated retinal repair.

With reference again to FIG. 3, the invisible, true sub-threshold photocoagulation phototherapy maximizes the therapeutic recruitment of the RPE through the concept of "maximize the affected surface area", in that all areas of RPE exposed to the laser irradiation are preserved, and available to contribute therapeutically. As discussed above with respect to FIG. 2, it is believed that conventional therapy creates a therapeutic ring around the burned or damaged tissue areas, whereas the present invention creates a therapeutic area without any burned or otherwise destroyed tissue.

Figure 4:
FIG. 4 is an illustration of a cross-sectional view of a diseased human retina before treatment with the present invention.
Figure 5:
FIG. 5 is a cross-sectional view similar to FIG. 10, illustrating the portion of the retina after treatment using the present invention.

With reference now to FIGS. 4 and 5, spectral-domain OCT imaging is shown in FIG. 4 of the macular and foveal area of the retina before treatment with the present invention. FIG. 5 is of the optical coherence tomography (OCT) image of the same macula and fovea after treatment using the present invention, using a 131 micrometer retinal spot, 5% duty cycle, 0.3 second pulse duration, 0.9 watt peak power placed throughout the area of macular thickening, including the fovea. It will be noted that the enlarged dark area to the left of the fovea depression (representing the pathologic retinal thickening of diabetic macular edema) is absent, as well as the fact that there is an absence of any laser-induced retinal damage. Such treatment simply would not be attainable with conventional techniques.

In another departure from conventional retinal photocoagulation, a low red to infrared laser light beam, such as from an 810 nm micropulsed diode laser, is used instead of an argon laser. It has been found that the 810 nm diode laser is minimally absorbed and negligibly scattered by intraretinal blood, cataract, vitreous hemorrhage and even severely edematous neurosensory retina. Differences in fundus coloration result primarily from differences in choroid pigmentation, and less of variation of the target RPE. Treatment in accordance with the present invention is thus simplified, requiring no adjustment in laser parameters for variations in macular thickening, intraretinal hemorrhage, and media opacity such as cataracts or fundus pigmentation, reducing the risk of error.

However, it is contemplated that the present invention could be utilized with micropulsed emissions of other wavelengths, such as the recently available 577 nm yellow and 532 nm green lasers, and others. The higher energies and different tissue absorption characteristic of shorter wavelength lasers may increase retinal burn risk, effectively narrowing the therapeutic window. In addition, the shorter wavelengths are more scattered by opaque ocular media, retinal hemorrhage and macular edema, potentially limiting usefulness and increasing the risk of retinal damage in certain clinical settings. Thus, a low red to infrared laser light beam is still preferred.

In fact, low power red and near-infrared laser exposure is known to positively affect many cell types, particularly normalizing the behavior of cells and pathological environments, such as diabetes, through a variety of intracellular photo-acceptors. Cell function, in cytokine expression, is normalized and inflammation reduced. By normalizing function of the viable RPE cells, the invention may induce changes in the expression of multiple factors physiologically as opposed to drug therapy that typically narrowly targets only a few post-cellular factors pharmacologically. The laser-induced physiologic alteration of RPE cytokine expression may account for the slower onset but long lasting benefits using the present invention. Furthermore, use of a physiologically invisible infrared or near-infrared laser wavelength is perceived as comfortable by the patient, and does not cause reactive pupillary constriction, allowing visualization of the ocular fundus and treatment of the retina to be performed without pharmacologic dilation of the patient pupil. This also eliminates the temporary of visual disability typically lasting many hours following pharmacologic pupillary dilation currently required for treatment with conventional laser photocoagulation. Currently, patient eye movement is a concern not only for creating the pattern of laser spots to treat the intended area, but also could result in exposure of conventional therapy to sensitive areas of the eye, such as the fovea, resulting in loss of vision or other complications.

The inventors have found that treatment in accordance with the invention of patients suffering from age-related macular degeneration (AMD) can slow the progress or even stop the progression of AMD. Further evidence of this restorative treatment effect is the inventor's finding that treatment can uniquely reduce the risk of vision loss in AMD due to choroidal neovascularization by 80%. Most of the patients have seen significant improvement in dynamic functional log MAR visual acuity and contrast visual acuity after the treatment in accordance with the invention, with some experiencing better vision. It is believed that this works by targeting, preserving, and "normalizing" (moving toward normal) function of the retinal pigment epithelium (RPE).

Treatment in accordance with the invention has also been shown to stop or reverse the manifestations of the diabetic retinopathy disease state without treatment-associated damage or adverse effects, despite the persistence of systemic diabetes mellitus. Studies published by the inventor have shown that the restorative effect of treatment can uniquely reduce the risk of progression of diabetic retinopathy by 85%. On this basis it is hypothesized that the invention might work by inducing a return to more normal cell function and cytokine expression in diabetes-affected RPE cells, analogous to hitting the "reset" button of an electronic device to restore the factory default settings.

Based on the above information and studies, SDM treatment may directly affect cytokine expression and heat shock protein (HSP) activation in the targeted tissue, particularly the retinal pigment epithelium (RPE) layer. Panretinal and panmacular SDM has been noted by the inventors to reduce the rate of progression of many retinal diseases, including severe non-proliferative and proliferative diabetic retinopathy, AMD, DME, etc. The known therapeutic treatment benefits of individuals having these retinal diseases, coupled with the absence of known adverse treatment effects, allows for consideration of early and preventative treatment, liberal application and retreatment as necessary. The reset theory also suggests that the invention may have application to many different types of RPE-mediated retinal disorders. In fact, the inventor has recently shown that panmacular treatment can significantly improve retinal function and health, retinal sensitivity, and dynamic log MAR visual acuity and contrast visual acuity in dry age-related macular degeneration, retinitis pigmentosa, cone-rod retinal degenerations, and Stargardt's disease where no other treatment has previously been found to do so.

Currently, retinal imaging and visual acuity testing guide management of chronic, progressive retinal diseases. As tissue and/or organ structural damage and vision loss are late disease manifestations, treatment instituted at this point must be intensive, often prolonged and expensive, and frequently fails to improve visual acuity and rarely restores normal vision. As the invention has been shown to be an effective treatment for a number of retinal disorders without adverse treatment effects, and by virtue of its safety and effectiveness, it can also be used to treat an eye to stop or delay the onset or symptoms of retinal diseases prophylactically or as a preventative treatment for such retinal diseases. Any treatment that improves retinal function, and thus health, should also reduce disease severity, progression, untoward events and visual loss. By beginning treatment early, prior to pathologic structural change, and maintaining the treatment benefit by regular functionally-guided retreatment, structural degeneration and visual loss might thus be delayed if not prevented. Even modest early reductions in the rate of disease progression may lead to significant long-term reductions and complications in visual loss. By mitigating the consequences of the primary defect, the course of disease may be muted, progression slowed, and complications and visual loss reduced. This is reflected in the inventor's studies, finding that treatment reduces the risk of progression and visual loss in diabetic retinopathy by 85% and AMD by 80%.

In accordance with the present invention, it is determined that a patient, and more particularly an eye of the patient, has a risk for a retinal disease. This may be before retinal imaging abnormalities are detectable. Such a determination may be accomplished by ascertaining if the patient is at risk for a chronic progressive retinopathy, including diabetes, a risk for age-related macular degeneration or retinitis pigmentosa. Alternatively, or additionally, results of a retinal examination or retinal test of the patient may be abnormal. A specific test, such as a retinal physiology test or a genetic test, may be conducted to establish that the patient has a risk for a retinal disease.

A laser light beam, that is sublethal and creates true subthreshold photocoagulation and retinal tissue, is generated and at least a portion of the retinal tissue is exposed to the generated laser light beam without damaging the exposed retinal or foveal tissue, so as to provide preventative and protective treatment of the retinal tissue of the eye. The treated retina may comprise the fovea, foveola, retinal pigment epithelium (RPE), choroid, choroidal neovascular membrane, subretinal fluid, macula, macular edema, parafovea, and/or perifovea. The laser light beam may be exposed to only a portion of the retina, or substantially the entire retina and fovea.

While most treatment effects appear to be long-lasting, if not permanent, clinical observations suggest that it can appear to wear off on occasion. Accordingly, the retina is periodically retreated. This may be done according to a set schedule or when it is determined that the retina of the patient is to be retreated, such as by periodically monitoring visual and/or retinal function or condition of the patient.

Figure 6:
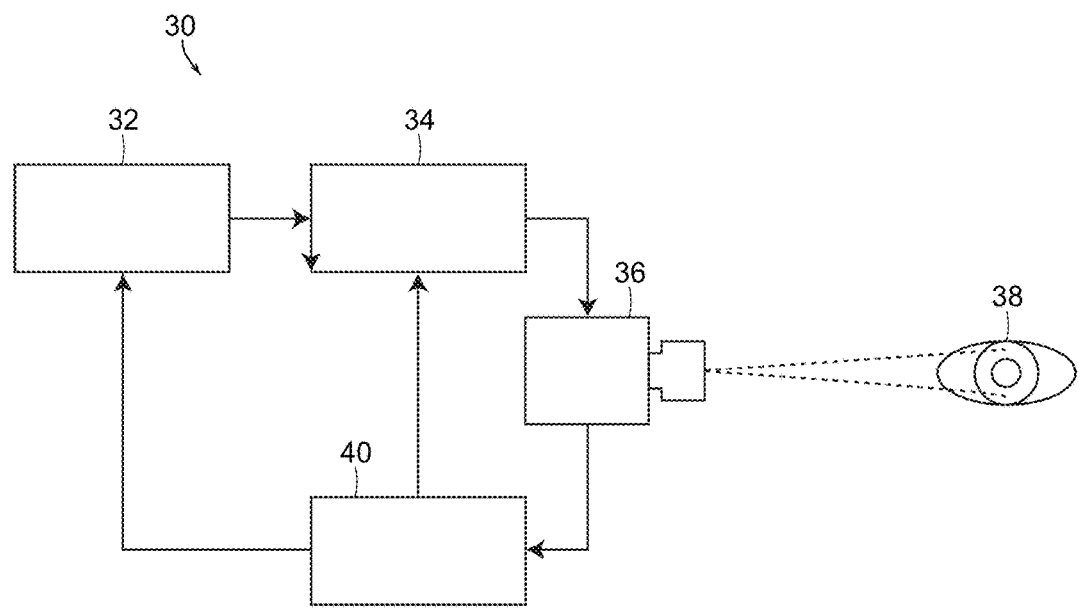
FIG. 6 is a diagrammatic view illustrating a system used for treating a retinal disease or disorder in accordance with the present invention.

With reference now to FIG. 6, a schematic diagram is shown of a system for realizing the process of the present invention. The system, generally referred to by the reference number 30, includes a laser console 32, such as for example the 810 nm near infrared micropulsed diode laser in the preferred embodiment. The laser generates a laser light beam which is passed through optics, such as an optical lens or mask, or a plurality of optical lenses and/or masks 34 as needed. The laser projector optics 34 pass the shaped light beam to a coaxial wide-field non-contact digital optical viewing system/camera 36 for projecting the laser beam light onto the eye 38 of the patient. It will be understood that the box labeled 36 can represent both the laser beam projector as well as a viewing system/camera, which might in reality comprise two different components in use. The viewing system/camera 36 provides feedback to a display monitor 40, which may also include the necessary computerized hardware, data input and controls, etc. for manipulating the laser 32, the optics 34, and/or the projection/viewing components 36.

As discussed above, current treatment requires the application of a large number of individual laser beam spots singly applied to the target tissue to be treated. These can number in the hundreds or even thousands for the desired treatment area. This is very time intensive and laborious.

Figure 7:
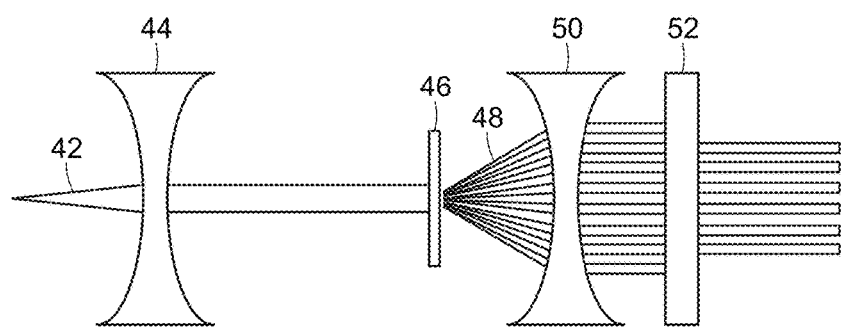
FIG. 7 is a diagrammatic view of an exemplary optical lens or mask used to generate a geometric pattern, in accordance with the present invention.

With reference now to FIG. 7, in one embodiment, the laser light beam 42 is passed through a collimator lens 44 and then through a mask 46. In a particularly preferred embodiment, the mask 46 comprises a diffraction grating. The mask/diffraction grating 46 produces a geometric object, or more typically a geometric pattern of simultaneously produced multiple laser spots or other geometric objects. This is represented by the multiple laser light beams labeled with reference number 48. Alternatively, the multiple laser spots may be generated by a plurality of fiber optic wires. Either method of generating laser spots allows for the creation of a very large number of laser spots simultaneously over a very wide treatment field, such as consisting of the entire retina. In fact, a very high number of laser spots, perhaps numbering in the hundreds even thousands or more could cover the entire ocular fundus and entire retina, including the macula and fovea, retinal blood vessels and optic nerve. The intent of the process in the present invention is to better ensure complete and total coverage and treatment, sparing none of the retina by the laser so as to improve vision.

Using optical features with a feature size on par with the wavelength of the laser employed, for example using a diffraction grating, it is possible to take advantage of quantum mechanical effects which permits simultaneous application of a very large number of laser spots for a very large target area. The individual spots produced by such diffraction gratings are all of a similar optical geometry to the input beam, with minimal power variation for each spot. The result is a plurality of laser spots with adequate irradiance to produce harmless yet effective treatment application, simultaneously over a large target area. The present invention also contemplates the use of other geometric objects and patterns generated by other diffractive optical elements.

The laser light passing through the mask 46 diffracts, producing a periodic pattern a distance away from the mask 46, shown by the laser beams labeled 48 in FIG. 7. The single laser beam 42 has thus been formed into multiple, up to hundreds or even thousands, of individual laser beams 48 so as to create the desired pattern of spots or other geometric objects. These laser beams 48 may be passed through additional lenses, collimators, etc. 50 and 52 in order to convey the laser beams and form the desired pattern on the patient's retina. Such additional lenses, collimators, etc. 50 and 52 can further transform and redirect the laser beams 48 as needed.

Arbitrary patterns can be constructed by controlling the shape, spacing and pattern of the optical mask 46. The pattern and exposure spots can be created and modified arbitrarily as desired according to application requirements by experts in the field of optical engineering. Photolithographic techniques, especially those developed in the field of semiconductor manufacturing, can be used to create the simultaneous geometric pattern of spots or other objects.

Although hundreds or even thousands of simultaneous laser spots could be generated and created and formed into patterns to be applied to the eye tissue, due to the requirements of not overheating the eye tissue, and particularly the eye lens, there are constraints on the number of treatment spots or beams which can be simultaneously used in accordance with the present invention. Each individual laser beam or spot requires a minimum average power over a train duration to be effective. However, at the same time, eye tissue cannot exceed certain temperature rises without becoming damaged. For example, there is a 4° C. restriction on the eye lens temperature rise which would set an upper limit on the average power that can be sent through the lens so as not to overheat and damage the lens of the eye. For example, using an 810 nm wavelength laser, the number of simultaneous spots generated and used could number from as few as 1 and up to approximately 100 when a 0.04 (4%) duty cycle and a total train duration of 0.3 seconds (300 milliseconds) is used for panretinal coverage. The water absorption increases as the wavelength is increased, resulting in heating over the long path length through the vitreous humor in front of the retina. For shorter wavelengths, e.g., 577 nm, the absorption coefficient in the RPE's melanin can be higher, and therefore the laser power can be lower. For example, at 577 nm, the power can be lowered by a factor of 4 for the invention to be effective. Accordingly, there can be as few as a single laser spot or up to approximately 400 laser spots when using the 577 nm wavelength laser light, while still not harming or damaging the eye.

The present invention can use a multitude of simultaneously generated therapeutic light beams or spots, such as numbering in the dozens or even hundreds, as the parameters and methodology of the present invention create therapeutically effective yet non-destructive and non-permanently damaging treatment, allowing the laser light spots to be applied to any portion of the retina, including the fovea, whereas conventional techniques are not able to use a large number of simultaneous laser spots, and are often restricted to only one treatment laser beam, in order to avoid accidental exposure of sensitive areas of the retina, such as the fovea, as these will be damaged from the exposure to conventional laser beam methodologies, which could cause loss of eyesight and other complications.

Figure 8:
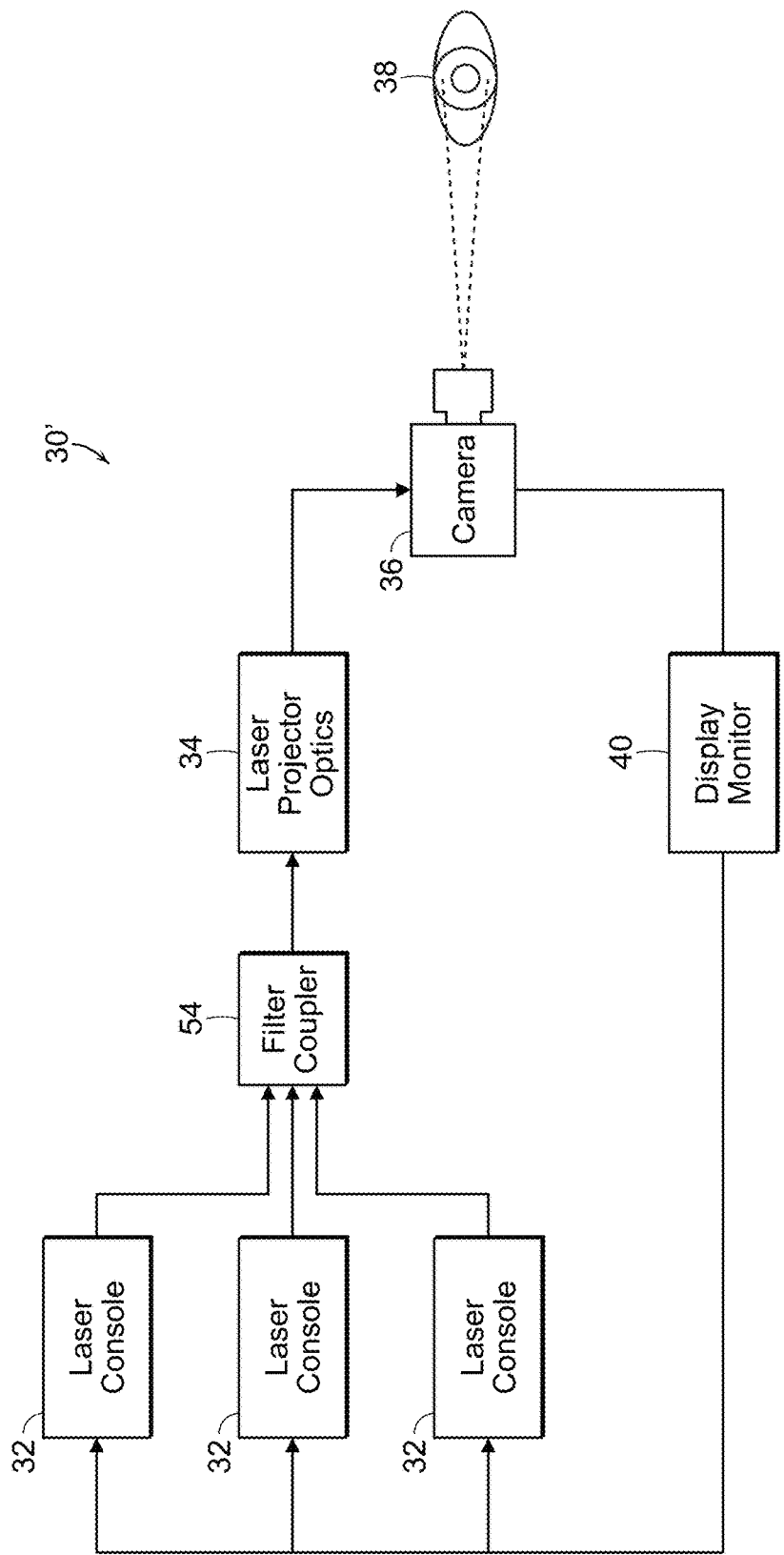
FIG. 8 is a diagrammatic view illustrating an alternate embodiment of a system used for treating a retinal disease or disorder in accordance with the present invention.

FIG. 8 illustrates diagrammatically a system which couples multiple light sources into the pattern-generating optical subassembly described above. Specifically, this system 30' is similar to the system 30 described in FIG. 6 above. The primary differences between the alternate system 30' and the earlier described system 30 is the inclusion of a plurality of laser consoles 32, the outputs of which are each fed into a fiber coupler 54. The fiber coupler produces a single output that is passed into the laser projector optics 34 as described in the earlier system. The coupling of the plurality of laser consoles 32 into a single optical fiber is achieved with a fiber coupler 54 as is known in the art. Other known mechanisms for combining multiple light sources are available and may be used to replace the fiber coupler described herein.

In this system 30' the multiple light sources 32 follow a similar path as described in the earlier system 30, i.e., collimated, diffracted, recollimated, and directed into the retina with a steering mechanism. In this alternate system 30' the diffractive element must function differently than described earlier depending upon the wavelength of light passing through, which results in a slightly varying pattern. The variation is linear with the wavelength of the light source being diffracted. In general, the difference in the diffraction angles is small enough that the different, overlapping patterns may be directed along the same optical path through the steering mechanism 36 to the retina 38 for treatment. The slight difference in the diffraction angles will affect how the steering pattern achieves coverage of the retina.

Since the resulting pattern will vary slightly for each wavelength, a sequential offsetting to achieve complete coverage will be different for each wavelength. This sequential offsetting can be accomplished in two modes. In the first mode, all wavelengths of light are applied simultaneously without identical coverage. An offsetting steering pattern to achieve complete coverage for one of the multiple wavelengths is used. Thus, while the light of the selected wavelength achieves complete coverage of the retina, the application of the other wavelengths achieves either incomplete or overlapping coverage of the retina. The second mode sequentially applies each light source of a varying wavelength with the proper steering pattern to achieve complete coverage of the retina for that particular wavelength. This mode excludes the possibility of simultaneous treatment using multiple wavelengths, but allows the optical method to achieve identical coverage for each wavelength. This avoids either incomplete or overlapping coverage for any of the optical wavelengths.

These modes may also be mixed and matched. For example, two wavelengths may be applied simultaneously with one wavelength achieving complete coverage and the other achieving incomplete or overlapping coverage, followed by a third wavelength applied sequentially and achieving complete coverage.

Figure 9:
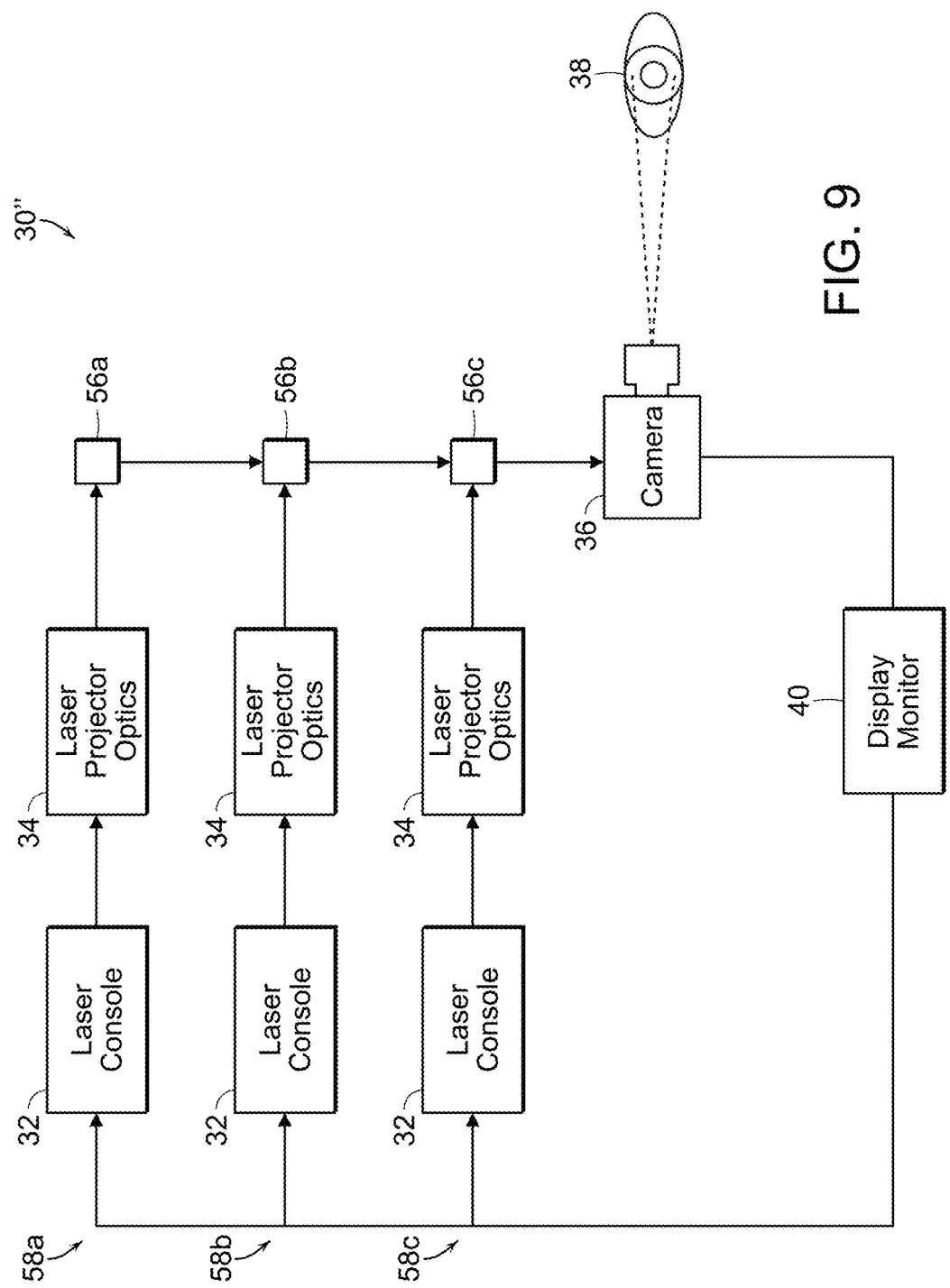
FIG. 9 is a diagrammatic view illustrating yet another alternate embodiment of a system used for treating a retinal disease or disorder in accordance with the present invention.

FIG. 9 illustrates diagrammatically yet another alternate embodiment of the inventive system 30". This system 30" is configured generally the same as the system 30 depicted in FIG. 6. The main difference resides in the inclusion of multiple pattern-generating subassembly channels tuned to a specific wavelength of the light source. Multiple laser consoles 32 are arranged in parallel with each one leading directly into its own laser projector optics 34. The laser projector optics of each channel 58a, 58b, 58c comprise a collimator 44, mask or diffraction grating 48 and recollimators 50, 52 as described in connection with FIG. 7 above—the entire set of optics tuned for the specific wavelength generated by the corresponding laser console 32. The output from each set of optics 34 is then directed to a beam splitter 56 for combination with the other wavelengths. It is known by those skilled in the art that a beam splitter used in reverse can be used to combine multiple beams of light into a single output.

The combined channel output from the final beam splitter 56c is then directed through the camera 36 which applies a steering mechanism to allow for complete coverage of the retina 38.

In this system 30" the optical elements for each channel are tuned to produce the exact specified pattern for that channel's wavelength. Consequently, when all channels are combined and properly aligned a single steering pattern may be used to achieve complete coverage of the retina for all wavelengths.

The system 30" may use as many channels 58a, 58b, 58c, etc. and beam splitters 56a, 56b, 56c, etc. as there are wavelengths of light being used in the treatment.

Implementation of the system 30" may take advantage of different symmetries to reduce the number of alignment constraints. For example, the proposed grid patterns are periodic in two dimensions and steered in two dimensions to achieve complete coverage. As a result, if the patterns for each channel are identical as specified, the actual pattern of each channel would not need to be aligned for the same steering pattern to achieve complete coverage for all wavelengths. Each channel would only need to be aligned optically to achieve an efficient combination.

In system 30", each channel begins with a light source 32, which could be from an optical fiber as in other embodiments of the pattern-generating subassembly. This light source 32 is directed to the optical assembly 34 for collimation, diffraction, recollimation and directed into the beam splitter which combines the channel with the main output.

The field of photobiology reveals that different biologic effects may be achieved by exposing target tissues to lasers of different wavelengths. The same may also be achieved by consecutively applying multiple lasers of either different or the same wavelength in sequence with variable time periods of separation and/or with different irradiant energies. The present invention anticipates the use of multiple laser, light or radiant wavelengths (or modes) applied simultaneously or in sequence to maximize or customize the desired treatment effects. This method also minimizes potential detrimental effects. The optical methods and systems illustrated and described above provide simultaneous or sequential application of multiple wavelengths.

Typically, the system of the present invention incorporates a guidance system to ensure complete and total retinal treatment with retinal photostimulation. This guidance system is to be distinguished from traditional retinal laser guidance systems that are employed to both direct treatment to a specific retinal location; and to direct treatment away from sensitive locations such as the fovea that would be damaged by conventional laser treatment, as the treatment method of the present invention is harmless, the entire retina, including the fovea and even optical nerve, can be treated. Moreover, protection against accidental visual loss by accidental patient movement is not a concern. Instead, patient movement would mainly affect the guidance in tracking of the application of the laser light to ensure adequate coverage. Fixation/tracking/registration systems consisting of a fixation target, tracking mechanism, and linked to system operation are common in many ophthalmic diagnostic systems and can be incorporated into the present invention.

In a particularly preferred embodiment, the geometric pattern of simultaneous laser spots is sequentially offset so as to achieve confluent and complete treatment of the retinal surface. Although a segment of the retina can be treated in accordance with the present invention, more ideally the entire retina will be treated within one treatment session. This is done in a time-saving manner by placing a plurality of spots over the entire ocular fundus at once. This pattern of simultaneous spots is scanned, shifted, or redirected as an entire array sequentially, so as to cover the entire retina in a single treatment session.

Figure 10:
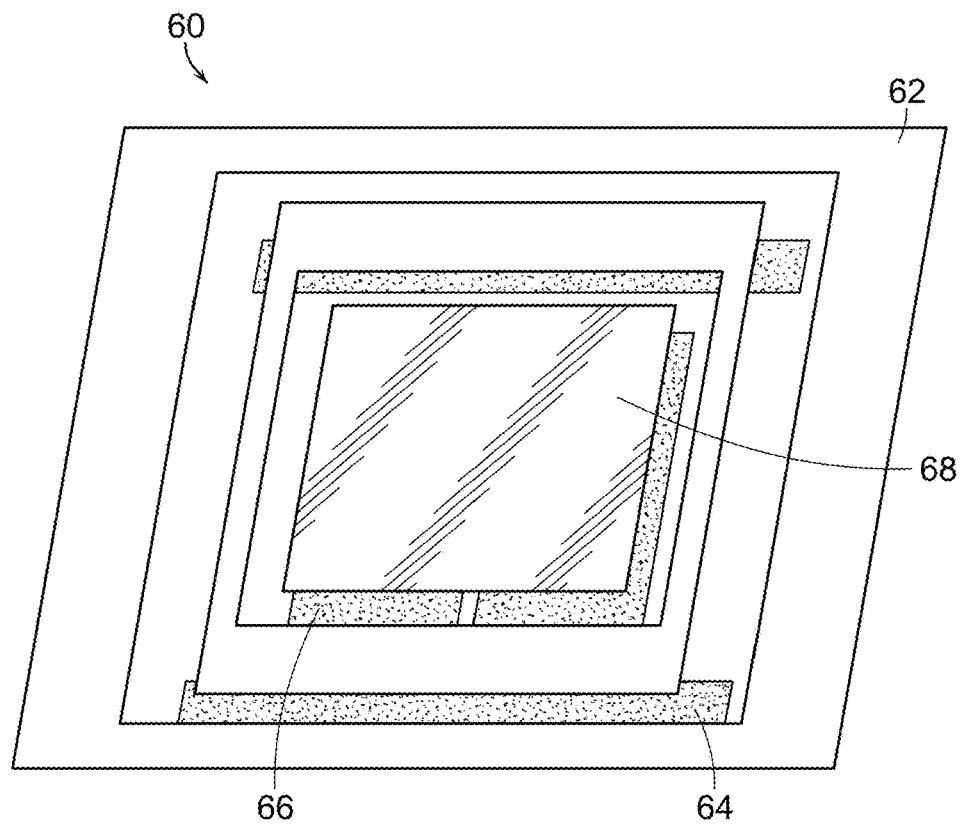
FIG. 10 is a top plan view of an optical scanning mechanism, used in accordance with the present invention.
Figure 11:
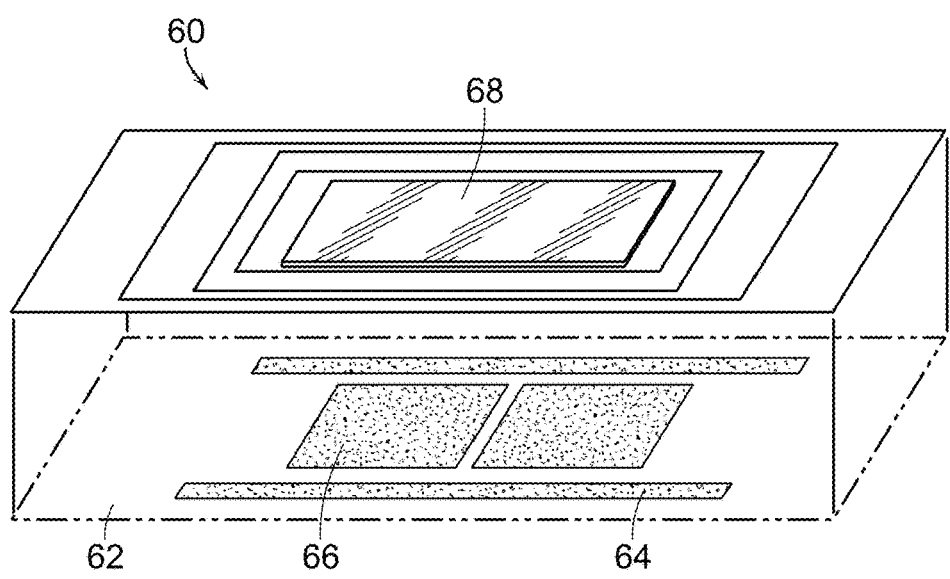
FIG. 11 is a partially exploded view of the optical scanning mechanism of FIG. 10, illustrating the various component parts thereof.

This can be done in a controlled manner using an optical scanning mechanism 60. FIGS. 10 and 11 illustrate an optical scanning mechanism 60 in the form of a MEMS mirror, having a base 62 with electronically actuated controllers 64 and 66 which serve to tilt and pan the mirror 68 as electricity is applied and removed thereto. Applying electricity to the controller 64 and 66 causes the mirror 68 to move, and thus the simultaneous pattern of laser spots or other geometric objects reflected thereon to move accordingly on the retina of the patient. This can be done, for example, in an automated fashion using electronic software program to adjust the optical scanning mechanism 60 until complete coverage of the retina, or at least the portion of the retina desired to be treated, is exposed to the phototherapy. The optical scanning mechanism may also be a small beam diameter scanning galvo mirror system, or similar system, such as that distributed by Thorlabs. Such a system is capable of scanning the lasers in the desired offsetting pattern.

Figure 12:
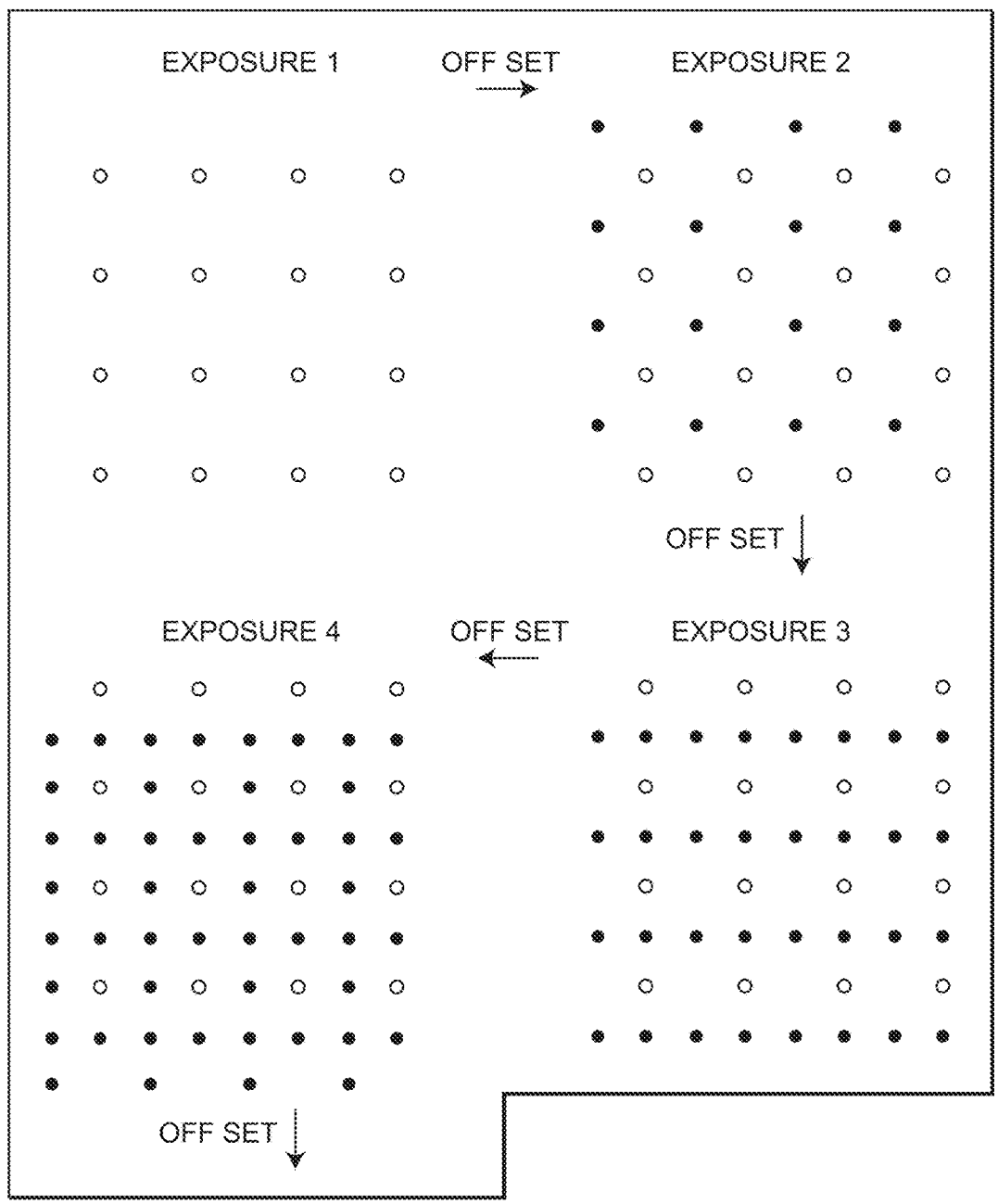
FIG. 12 illustrates controlled offset of exposure of an exemplary geometric pattern grid of laser spots to treat the retina.

Since the parameters of the present invention dictate that the applied radiant energy or laser light is not destructive or damaging, the geometric pattern of laser spots, for example, can be overlapped without destroying the tissue or creating any permanent damage. However, in a particularly preferred embodiment, as illustrated in FIG. 12, the pattern of spots are offset at each exposure so as to create space between the immediately previous exposure to allow heat dissipation and prevent the possibility of heat damage or tissue destruction. Thus, as illustrated in FIG. 12, the pattern, illustrated for exemplary purposes as a grid of sixteen spots, is offset each exposure such that the laser spots occupy a different space than previous exposures. It will be understood that the diagrammatic use of circles or empty dots as well as filled dots are for diagrammatic purposes only to illustrate previous and subsequent exposures of the pattern of spots to the area, in accordance with the present invention. The spacing of the laser spots prevents overheating and damage to the tissue. It will be understood that this occurs until the entire retina, the preferred methodology, has received phototherapy, or until the desired effect is attained. This can be done, for example, by applying electrostatic torque to a micromachined mirror, as illustrated in FIGS. 10 and 11. By combining the use of small retina laser spots separated by exposure free areas, prevents heat accumulation, and grids with a large number of spots per side, it is possible to atraumatically and invisibly treat large target areas with short exposure durations far more rapidly than is possible with current technologies. In this manner, a low-density treatment, such as illustrated in FIG. 3A, can become a high-density treatment, as illustrated in FIG. 3B.

By rapidly and sequentially repeating redirection or offsetting of the entire simultaneously applied grid array of spots or geometric objects, complete coverage of the target, such as a human retina, can be achieved rapidly without thermal tissue injury. This offsetting can be determined algorithmically to ensure the fastest treatment time and least risk of damage due to thermal tissue, depending on laser parameters and desired application. The following has been modeled using the Fraunhoffer Approximation. With a mask having a nine by nine square lattice, with an aperture radius 9 µm, an aperture spacing of 600 µm, using a 890 nm wavelength laser, with a mask-lens separation of 75 mm, and secondary mask size of 2.5 mm by 2.5 mm, the following parameters will yield a grid having nineteen spots per side separated by 133 µm with a spot size radius of 6 µm. The number of exposures "m" required to treat (cover confluently with small spot applications) given desired area side-length "A", given output pattern spots per square side "n", separation between spots "R", spot radius "r" and desired square side length to treat area "A", can be given by the following formula:

$$m = \frac{A}{nR}\text{floor}\left(\frac{R}{2r}\right)^2$$

With the foregoing setup, one can calculate the number of operations m needed to treat different field areas of exposure. For example, a 3 mm×3 mm area, which is useful for treatments, would require 98 offsetting operations, requiring a treatment time of approximately thirty seconds. Another example would be a 3 cm×3 cm area, representing the entire human retinal surface. For such a large treatment area, a much larger secondary mask size of 25 mm by 25 mm could be used, yielding a treatment grid of 190 spots per side separated by 133 µm with a spot size radius of 6 µm. Since the secondary mask size was increased by the same factor as the desired treatment area, the number of offsetting operations of approximately 98, and thus treatment time of approximately thirty seconds, is constant. These treatment times represent at least ten to thirty times reduction in treatment times compared to current methods of sequential individual laser spot applications. Field sizes of 3 mm would, for example, allow treatment of the entire human macula in a single exposure, useful for treatment of common blinding conditions such as diabetic macular edema and age-related macular degeneration. Performing the entire 98 sequential offsettings would ensure entire coverage of the macula.

Of course, the number and size of retinal spots produced in a simultaneous pattern array can be easily and highly varied such that the number of sequential offsetting operations required to complete treatment can be easily adjusted depending on the therapeutic requirements of the given application.

Furthermore, by virtue of the small apertures employed in the diffraction grating or mask, quantum mechanical behavior may be observed which allows for arbitrary distribution of the laser input energy. This would allow for the generation of any arbitrary geometric shapes or patterns, such as a plurality of spots in grid pattern, lines, or any other desired pattern. Other methods of generating geometric shapes or patterns, such as using multiple fiber optical fibers or microlenses, could also be used in the present invention. Time savings from the use of simultaneous projection of geometric shapes or patterns permits the treatment fields of novel size, such as the 1.2 cm^2 area to accomplish whole-retinal treatment, in a single clinical setting or treatment session.

Figure 13:
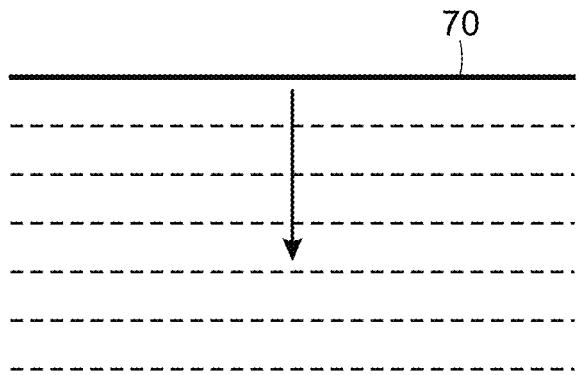
FIG. 13 is a diagrammatic view illustrating the units of a geometric object in the form of a line controllably scanned to treat an area of the retina.
Figure 14:
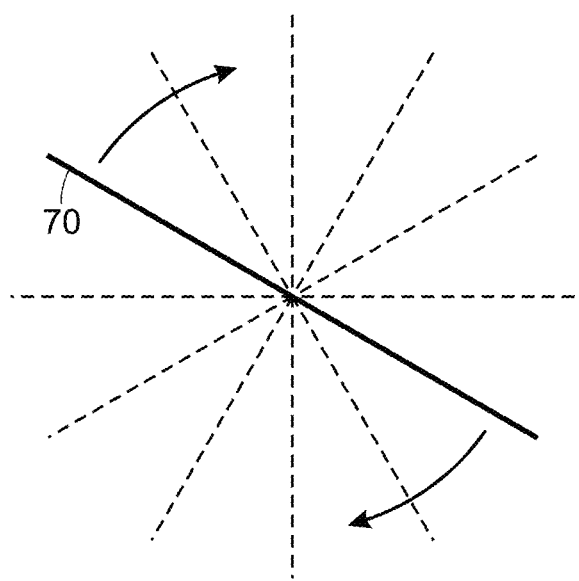
FIG. 14 is a diagrammatic view similar to FIG. 13, but illustrating the geometric line or bar rotated to treat an area of the retina.

With reference now to FIG. 14, instead of a geometric pattern of small laser spots, the present invention contemplates use of other geometric objects or patterns. For example, a single line 70 of laser light, formed by the continuously or by means of a series of closely spaced spots, can be created. An offsetting optical scanning mechanism can be used to sequentially scan the line over an area, illustrated by the downward arrow in FIG. 13.

With reference now to FIG. 14, the same geometric object of a line 70 can be rotated, as illustrated by the arrows, so as to create a circular field of phototherapy. The potential negative of this approach, however, is that the central area will be repeatedly exposed, and could reach unacceptable temperatures. This could be overcome, however, by increasing the time between exposures, or creating a gap in the line such that the central area is not exposed.

Power limitations in current micropulsed diode lasers require fairly long exposure duration. The longer the exposure, the more important the center-spot heat dissipating ability toward the unexposed tissue at the margins of the laser spot and toward the underlying choriocapillaris as in the retina. Thus, the micropulsed laser light beam of an 810 nm diode laser should have an exposure envelope duration of 500 milliseconds or less, and preferably approximately 300 milliseconds. Of course, if micropulsed diode lasers become more powerful, the exposure duration should be lessened accordingly.

Aside from power limitations, another parameter of the present invention is the duty cycle, or the frequency of the train of micropulses, or the length of the thermal relaxation time between consecutive pulses. It has been found that the use of a 10% duty cycle or higher adjusted to deliver micropulsed laser at similar irradiance at similar MPE levels significantly increase the risk of lethal cell injury, particularly in darker fundi. However, duty cycles of less than 10%, and preferably 5% or less demonstrate adequate thermal rise and treatment at the level of the MPE cell to stimulate a biological response, but remain below the level expected to produce lethal cell injury, even in darkly pigmented fundi. The lower the duty cycle, however, the exposure envelope duration increases, and in some instances can exceed 500 milliseconds.

Each micropulse lasts a fraction of a millisecond, typically between 50 microseconds to 100 microseconds in duration. Thus, for the exposure envelope duration of 300-500 milliseconds, and at a duty cycle of less than 5%, there is a significant amount of wasted time between micropulses to allow the thermal relaxation time between consecutive pulses. Typically, a delay of between 1 and 3 milliseconds, and preferably approximately 2 milliseconds, of thermal relaxation time is needed between consecutive pulses. For adequate treatment, the retinal cells are typically exposed or hit between 50-200 times, and preferably between 75-150 at each location, and with the 1-3 milliseconds of relaxation or interval time, the total time in accordance with the embodiments described above to treat a given area, or more particularly the locations on the retina which are being exposed to the laser spots is between 200 milliseconds and 500 milliseconds on average. The thermal relaxation time is required so as not to overheat the cells within that location or spot and so as to prevent the cells from being damaged or destroyed. While time periods of 200-500 milliseconds do not seem long, given the small size of the laser spots and the need to treat a relatively large area of the retina, treating the entire macula or the entire retina can take a significant amount of time, particularly for a patient who is undergoing treatment.

Accordingly, the present invention in a particularly preferred embodiment utilizes the interval between consecutive laser light applications to the same location (typically between 1 to 3 milliseconds) to apply the laser light to a second treatment area, or additional areas, of the retina and/or fovea that is spaced apart from the first treatment area. The laser beams are returned to the first treatment location, or previous treatment locations, within the predetermined interval of time so as to provide sufficient thermal relaxation time between consecutive pulses, yet also sufficiently treat the cells in those locations or areas properly by sufficiently increasing the temperature of those cells over time by repeatedly applying the laser light to that location in order to achieve the desired therapeutic benefits of the invention.

It is important to return to a previously treated location within 1-3 milliseconds, and preferably approximately 2 milliseconds, to allow the area to cool down sufficiently during that time, but also to treat it within the necessary window of time. For example, one cannot wait one or two seconds and then return to a previously treated area that has not yet received the full treatment necessary, as the treatment will not be as effective or perhaps not effective at all. However, during that interval of time, typically approximately 2 milliseconds, at least one other area, and typically multiple areas, can be treated with a laser light application as the laser light pulses are typically 50 seconds to 100 microseconds in duration. The number of additional areas which can be treated is limited only by the micopulse duration and the ability to controllably move the laser light beams from one area to another. Currently, approximately four additional areas which are sufficiently spaced apart from one another can be treated during the thermal relaxation intervals beginning with a first treatment area. Thus, multiple areas can be treated, at least partially, during the 200-500 millisecond exposure envelope for the first area. Thus, in a single interval of time, instead of only 100 simultaneous light spots being applied to a treatment area, approximately 500 light spots can be applied during that interval of time in different treatment areas. This would be the case, for example, for a laser light beam having a wavelength of 810 nm. For shorter wavelengths, such as 57 nm, even a greater number of individual locations can be exposed to the laser beams to create light spots. Thus, instead of a maximum of approximately 400 simultaneous spots, approximately 2,000 spots could be covered during the interval between micropulse treatments to a given area or location.

As mentioned above, typically each location has between 50-200, and more typically between 75-150, light applications applied thereto over the course of the exposure envelope duration (typically 200-500 milliseconds) to achieve the desired treatment. In accordance with an embodiment of the present invention, the laser light would be reapplied to previously treated areas in sequence during the relaxation time intervals for each area or location. This would occur repeatedly until a predetermined number of laser light applications to each area to be treated have been achieved.

Figure 15A:
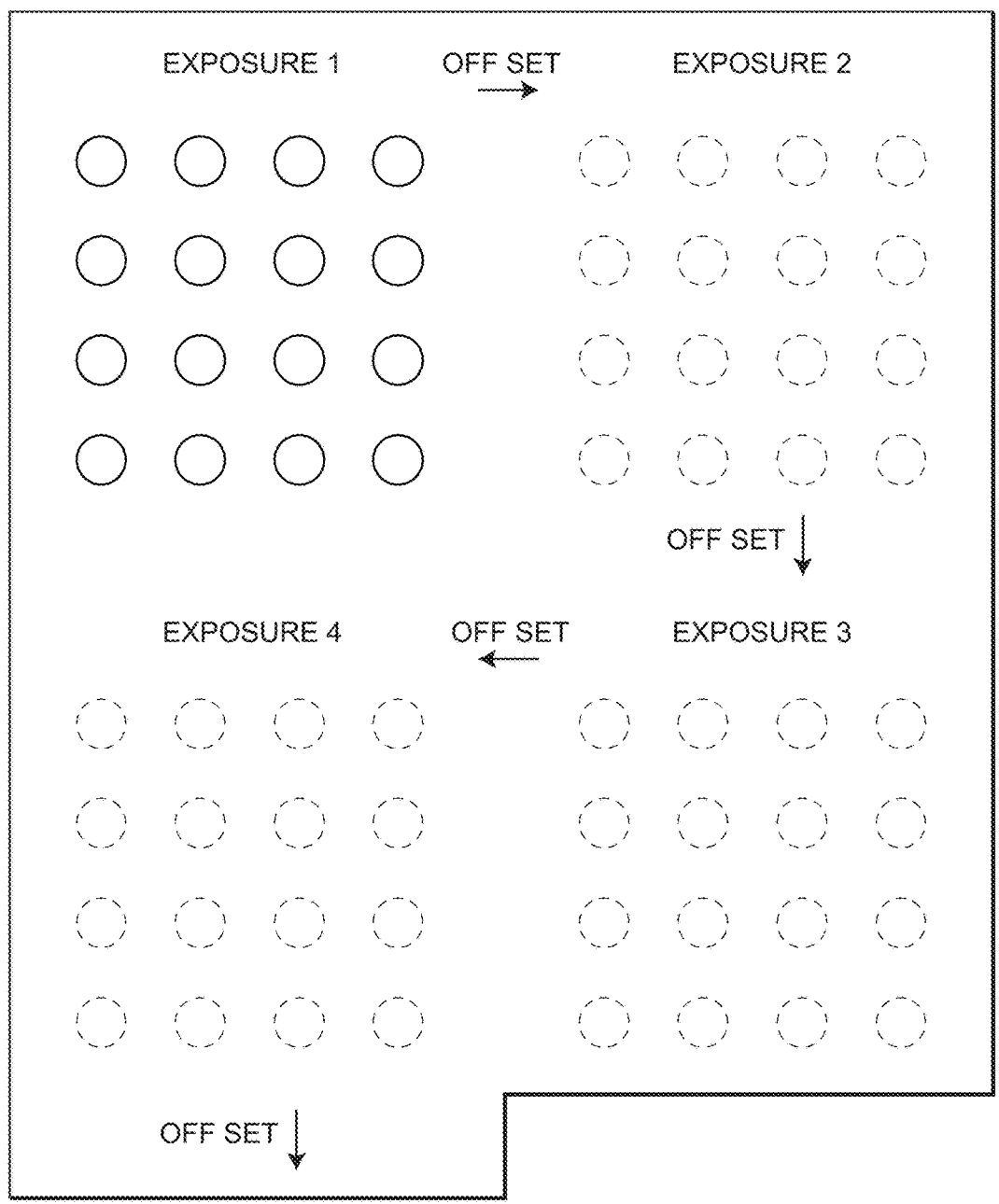
FIGS. 15A-15D are diagrammatic views illustrating the application of laser light to different treatment areas during a predetermined interval of time, within a single treatment session, and reapplying the laser light to previously treated areas, in accordance with the present invention.
Figure 15B:
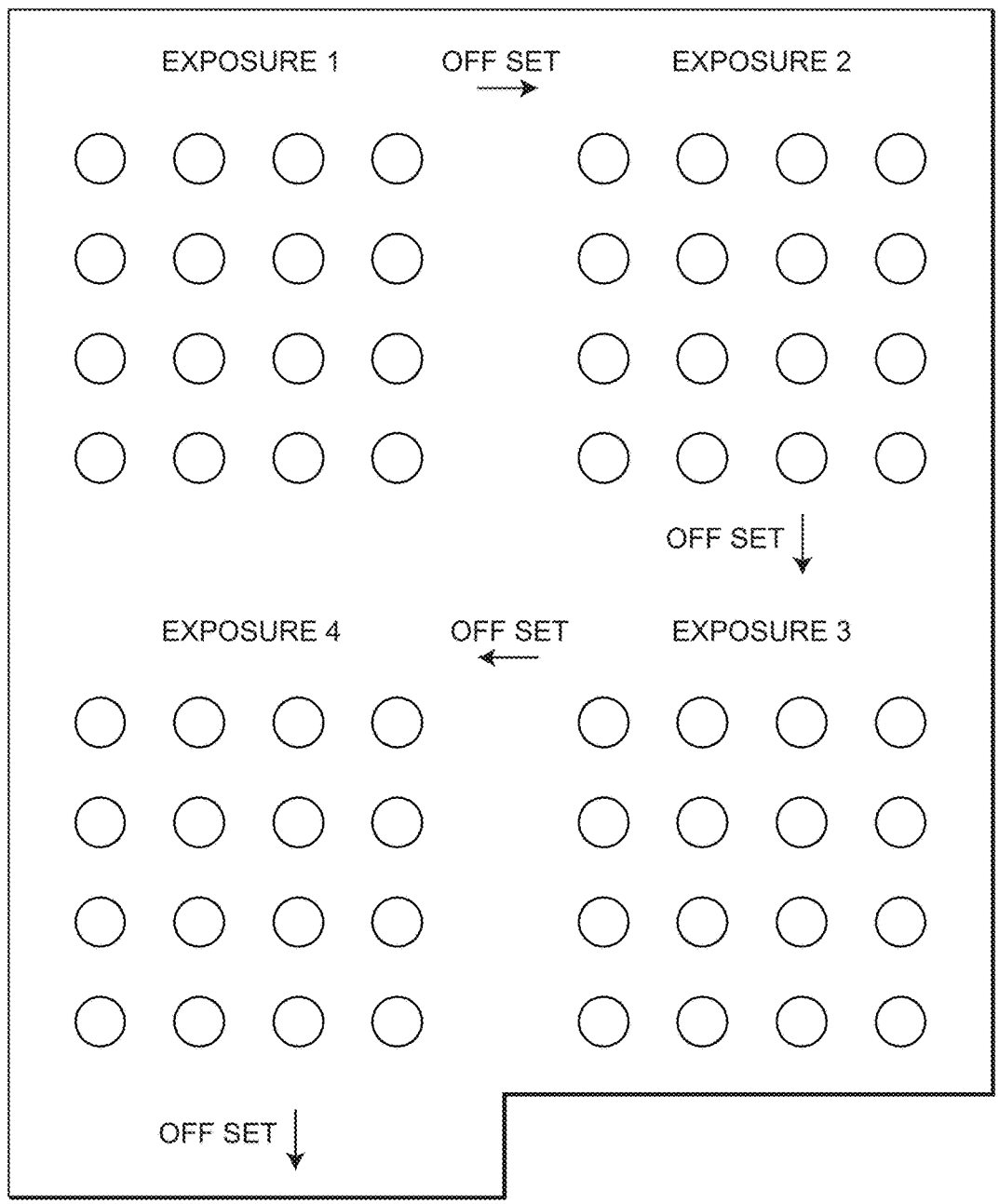
Figure 15C:
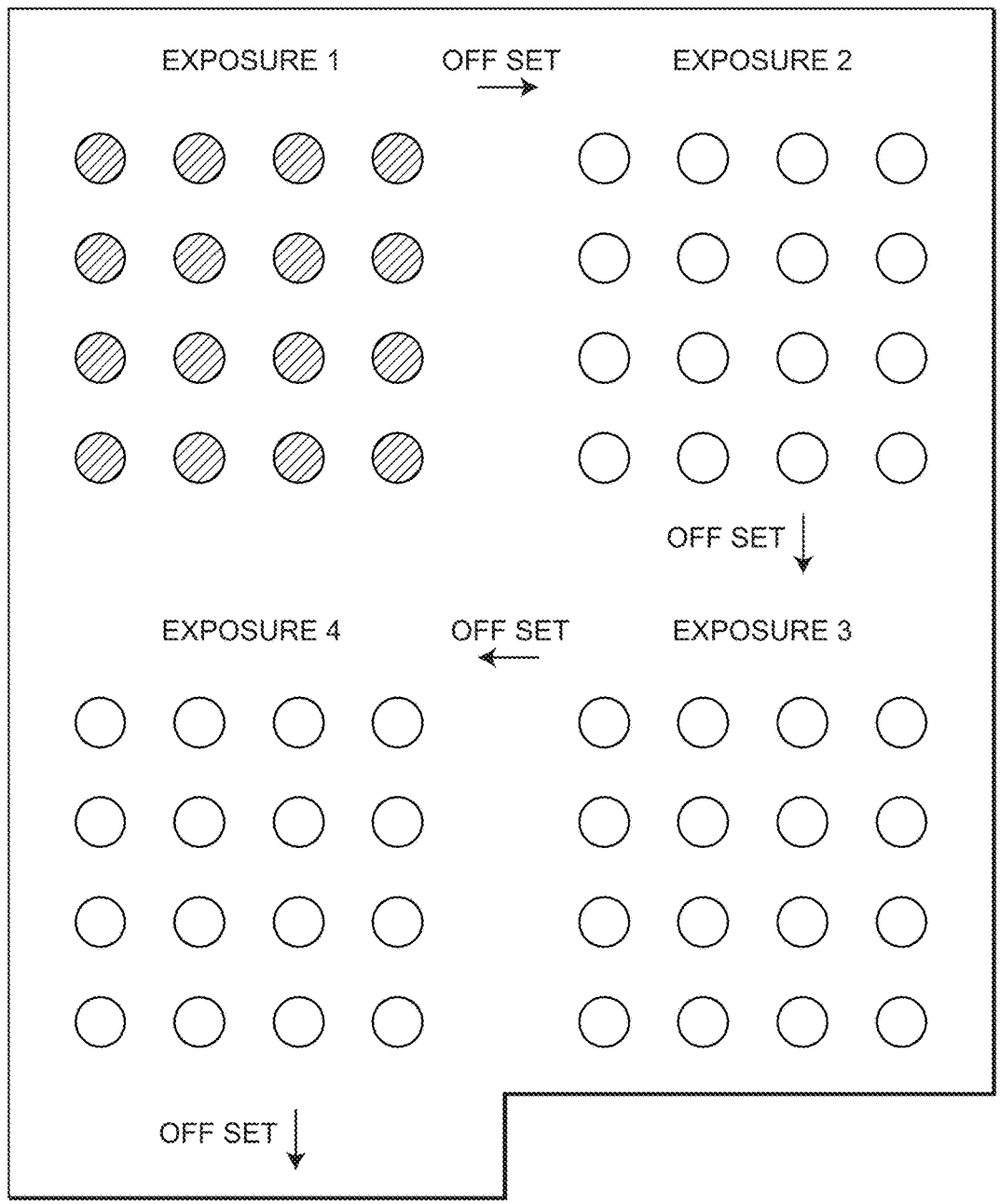
Figure 15D:
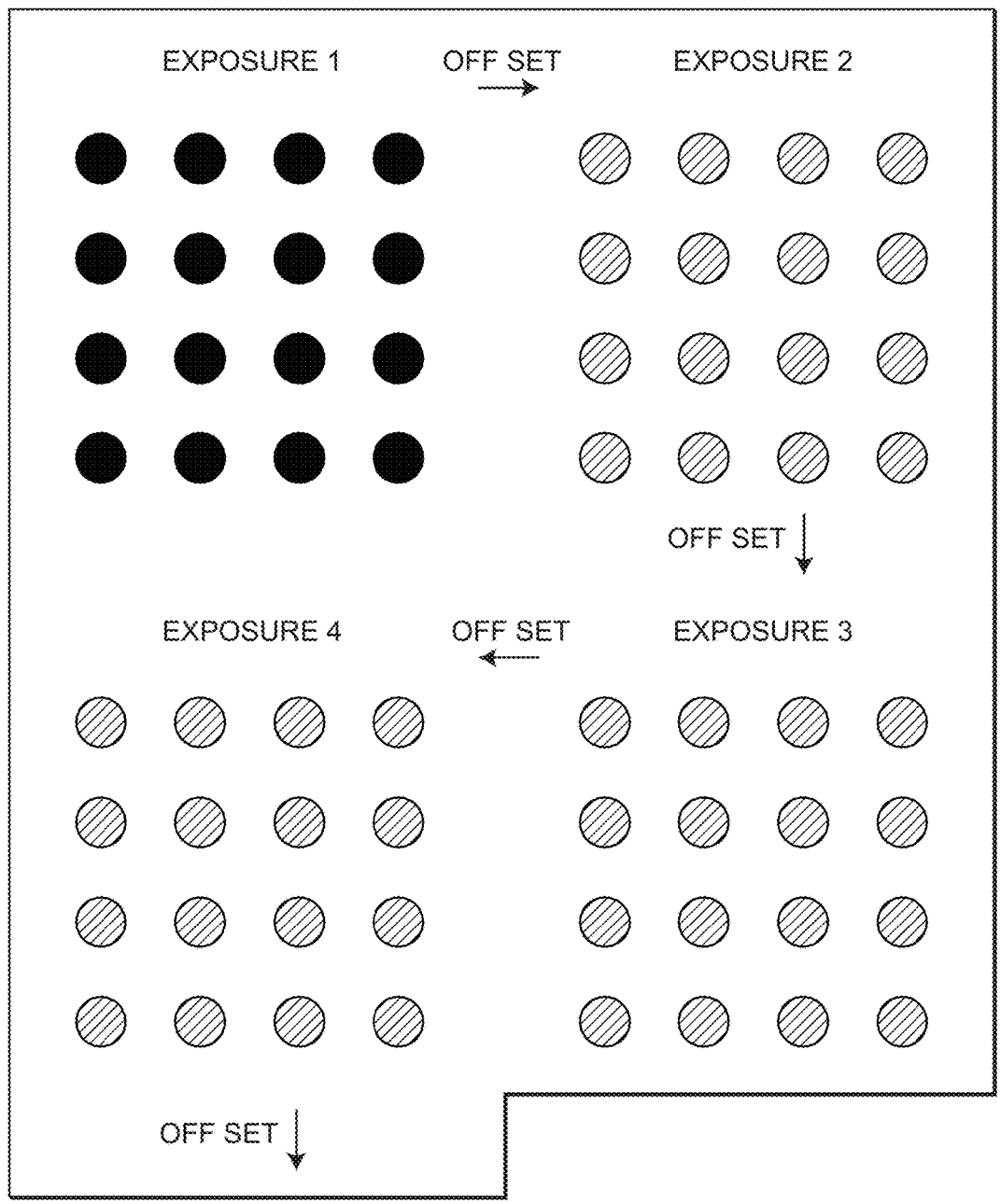

This is diagrammatically illustrated in FIGS. 15A-15D. FIG. 15A illustrates with solid circles a first area having laser light applied thereto as a first application. The laser beams are offset or microshifted to a second exposure area, followed by a third exposure area and a fourth exposure area, as illustrated in FIG. 15B, until the locations in the first exposure area need to be retreated by having laser light applied thereto again within the thermal relaxation time interval. The locations within the first exposure area would then have laser light reapplied thereto, as illustrated in FIG. 15C. Secondary or subsequent exposures would occur in each exposure area, as illustrated in FIG. 15D by the increasingly shaded dots or circles until the desired number of exposures or hits or light applications had been achieved to therapeutically treat these areas, diagrammatically illustrated by the blackened circles in exposure area 1 in FIG. 15D. When a first or previous exposure area has been completed treated, this enables the system to add an additional exposure area, which process is repeated until the entire area of retina to be treated has been fully treated. It should be understood that the use of solid circles, broken line circles, partially shaded circles, and fully shaded circles are for explanatory purposes only, as in fact the exposure of the laser light in accordance with the present invention is invisible and non-detectable to both the human eye as well as known detection devices and techniques.

Adjacent exposure areas must be separated by at least a predetermined minimum distance to avoid thermal tissue damage. Such distance is at least 0.5 diameter away from the immediately preceding treated location or area, and more preferably between 1-2 diameters away. Such spacing relates to the actually treated locations in a previous exposure area. It is contemplated by the present invention that a relatively large area may actually include multiple exposure areas therein which are offset in a different manner than that illustrated in FIG. 15. For example, the exposure areas could comprise the thin lines illustrated in FIGS. 13 and 14, which would be repeatedly exposed in sequence until all of the necessary areas were fully exposed and treated. In accordance with the present invention, this can comprise a limited area of the retina, the entire macula or panmacular treatment, or the entire retina, including the fovea. However, due to the methodology of the present invention, the time required to treat that area of the retina to be treated or the entire retina is significantly reduced, such as by a factor of 4 or 5 times, such that a single treatment session takes much less time for the medical provider and the patient need not be in discomfort for as long of a period of time.

Figure 16:
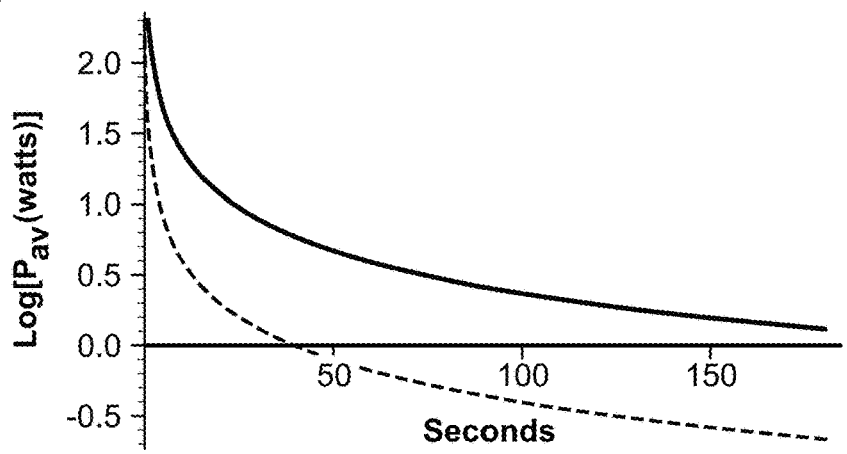
FIGS. 16-18 are graphs depicting the relationship of treatment power and time in accordance with embodiments of the present invention.
Figure 17:
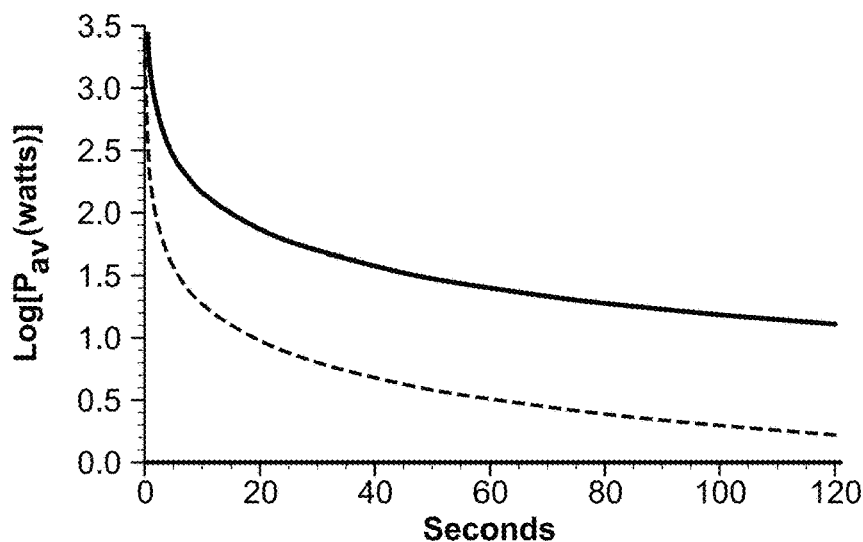
Figure 18:
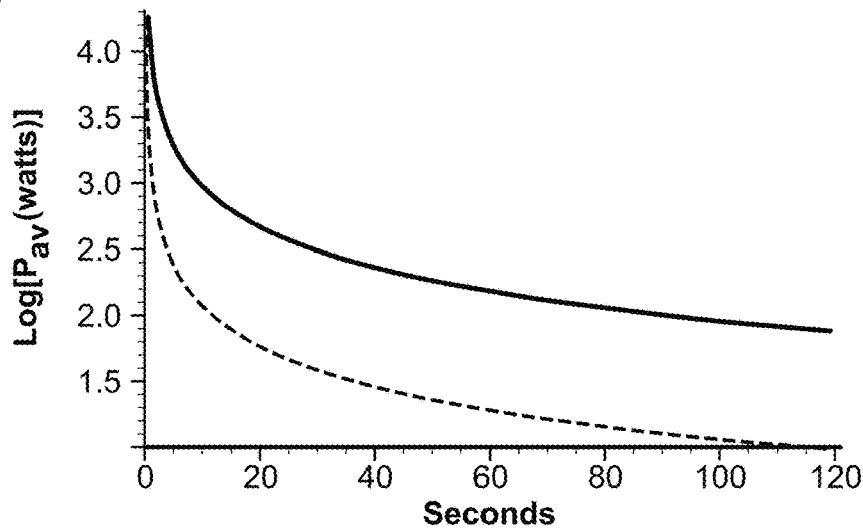

In accordance with this embodiment of the invention of applying one or more treatment beams to the retina at once, and moving the treatment beams to a series of new locations, then bringing the beams back to retreat the same location or area repeatedly has been found to also require less power compared to the methodology of keeping the laser beams in the same locations or area during the entire exposure envelope duration. With reference to FIGS. 16-18, there is a linear relationship between the pulse length and the power necessary, but there is a logarithmic relationship between the heat generated.

With reference to FIG. 16, a graph is provided wherein the x-axis represents the Log of the average power in watts and the y-axis represents the treatment time, in seconds. The lower curve is for panmacular treatment and the upper curve is for panretinal treatment. This would be for a laser light beam having a micropulse time of 50 microseconds, a period of 2 milliseconds period of time between pulses, and duration of train on a spot of 300 milliseconds. The areas of each retinal spot are 100 microns, and the laser power for these 100 micron retinal spots is 0.74 watts. The panmacular area is 0.55 $CM^2$, requiring 7,000 panmacular spots total, and the panretinal area is 3.30 $CM^2$, requiring 42,000 laser spots for full coverage. Each RPE spot requires a minimum energy in order for its reset mechanism to be adequately activated, in accordance with the present invention, namely, 38.85 joules for panmacular and 233.1 joules for panretinal. As would be expected, the shorter the treatment time, the larger the required average power. However, there is an upper limit on the allowable average power, which limits how short the treatment time can be.

As mentioned above, there are not only power constraints with respect to the laser light available and used, but also the amount of power that can be applied to the eye without damaging eye tissue. For example, temperature rise in the lens of the eye is limited, such as between 4° C. so as not to overheat and damage the lens, such as causing cataracts. Thus, an average power of 7.52 watts could elevate the lens temperature to approximately 4° C. This limitation in power increases the minimum treatment time.

However, with reference to FIG. 17, the total power per pulse required is less in the microshift case of repeatedly and sequentially moving the laser spots and returning to prior treated locations, so that the total energy delivered and the total average power during the treatment time is the same. FIGS. 17 and 18 show how the total power depends on treatment time. This is displayed in FIG. 17 for panmacular treatment, and in FIG. 18 for panretinal treatment. The upper, solid line or curve represents the embodiment where there are no microshifts taking advantage of the thermal relaxation time interval, such as described and illustrated in FIG. 12, whereas the lower dashed line represents the situation for such microshifts, as described and illustrated in FIG. 15. FIGS. 17 and 18 show that for a given treatment time, the peak total power is less with microshifts than without microshifts. This means that less power is required for a given treatment time using the microshifting embodiment of the present invention. Alternatively, the allowable peak power can be advantageously used, reducing the overall treatment time.

Thus, in accordance with FIGS. 16-18, a log power of 1.0 (10 watts) would require a total treatment time of 20 seconds using the microshifting embodiment of the present invention, as described herein. It would take more than 2 minutes of time without the microshifts, and instead leaving the micropulsed light beams in the same location or area during the entire treatment envelope duration. There is a minimum treatment time according to the wattage. However, this treatment time with microshifting is much less than without microshifting. As the laser power required is much less with the microshifting, it is possible to increase the power in some instances in order to reduce the treatment time for a given desired retinal treatment area. The product of the treatment time and the average power is fixed for a given treatment area in order to achieve the therapeutic treatment in accordance with the present invention. This could be implemented, for example, by applying a higher number of therapeutic laser light beams or spots simultaneously at a reduced power. Of course, since the parameters of the laser light are selected to be therapeutically effective yet not destructive or permanently damaging to the cells, no guidance or tracking beams are required, only the treatment beams as all areas of the retina, including the fovea, can be treated in accordance with the present invention. In fact, in a particularly preferred embodiment, the entire retina, including the fovea, is treated in accordance with the present invention, which is simply not possible using conventional techniques.

Although the present invention is described for use in connection with a micropulsed laser, theoretically a continuous wave laser could potentially be used instead of a micropulsed laser. However, with the continuous wave laser, there is concern of overheating as the laser is moved from location to location in that the laser does not stop and there could be heat leakage and overheating between treatment areas. Thus, while it is theoretically possible to use a continuous wave laser, in practice it is not ideal and the micropulsed laser is preferred.

Due to the unique characteristics of the present invention, allowing a single set of optimized laser parameters, which are not significantly influenced by media opacity, retinal thickening, or fundus pigmentation, a simplified user interface is permitted. While the operating controls could be presented and function in many different ways, the system permits a very simplified user interface that might employ only two control functions. That is, an "activate" button, wherein a single depression of this button while in "standby" would actuate and initiate treatment. A depression of this button during treatment would allow for premature halting of the treatment, and a return to "standby" mode. The activity of the machine could be identified and displayed, such as by an LED adjacent to or within the button. A second controlled function could be a "field size" knob. A single depression of this button could program the unit to produce, for example, a 3 mm focal or a "macular" field spot. A second depression of this knob could program the unit to produce a 6 mm or "posterior pole" spot. A third depression of this knob could program the unit to produce a "pan retinal" or approximately 160°-220° panoramic retinal spot or coverage area. Manual turning of this knob could produce various spot field sizes therebetween. Within each field size, the density and intensity of treatment would be identical. Variation of the field size would be produced by optical or mechanical masking or apertures, such as the iris or LCD apertures described below.

Fixation software could monitor the displayed image of the ocular fundus. Prior to initiating treatment of a fundus landmark, such as the optic nerve, or any part or feature of either eye of the patient (assuming orthophoria), could be marked by the operator on the display screen. Treatment could be initiated and the software would monitor the fundus image or any other image-registered to any part of either eye of the patient (assuming orthophoria) to ensure adequate fixation. A break in fixation would automatically interrupt treatment. A break in fixation could be detected optically; or by interruption of low energy infrared beams projected parallel to and at the outer margins of the treatment beam by the edge of the pupil. Treatment would automatically resume toward completion as soon as fixation was established. At the conclusion of treatment, determined by completion of confluent delivery of the desired laser energy to the target, the unit would automatically terminate exposure and default to the "on" or "standby" mode. Due to unique properties of this treatment, fixation interruption would not cause harm or risk patient injury, but only prolong the treatment session.

The laser could be projected via a wide field non-contact lens to the ocular fundus. Customized direction of the laser fields or particular target or area of the ocular fundus other than the central area could be accomplished by an operator joy stick or eccentric patient gaze. The laser delivery optics could be coupled coaxially to a wide field non-contact digital ocular fundus viewing system. The image of the ocular fundus produced could be displayed on a video monitor visible to the laser operator. Maintenance of a clear and focused image of the ocular fundus could be facilitated by a joy stick on the camera assembly manually directed by the operator. Alternatively, addition of a target registration and tracking system to the camera software would result in a completely automated treatment system.

A fixation image could be coaxially displayed to the patient to facilitate ocular alignment. This image would change in shape and size, color, intensity, blink or oscillation rate or other regular or continuous modification during treatment to avoid photoreceptor exhaustion, patient fatigue and facilitate good fixation.

Figure 19:
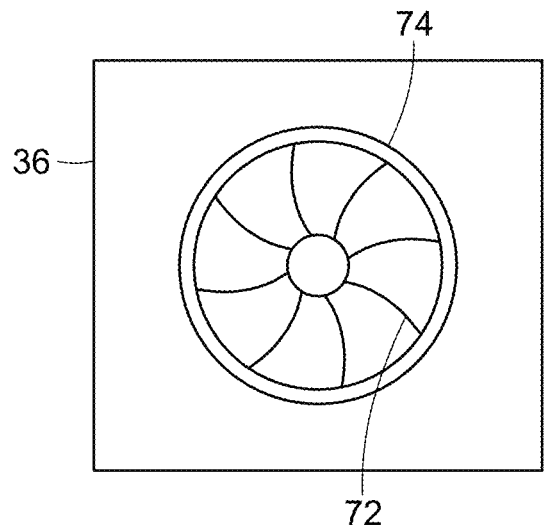
FIG. 19 is a front view of a camera including an iris aperture of the present invention.
Figure 20:
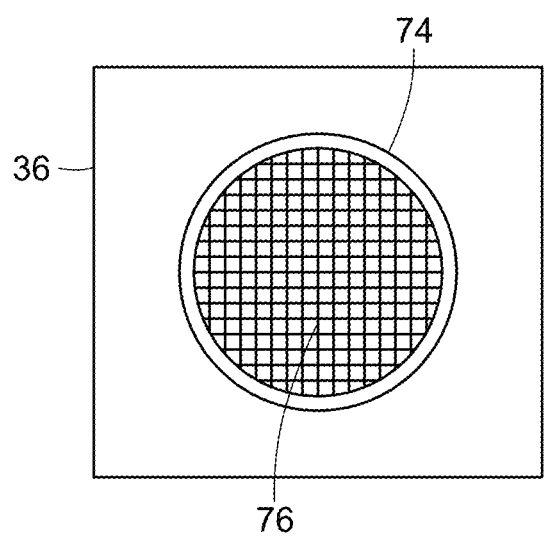
FIG. 20 is a front view of a camera including an LCD aperture of the present invention.

The invention described herein is generally safe for panretinal and/or trans-foveal treatment. However, it is possible that a user, i.e., surgeon, preparing to limit treatment to a particular area of the retina where disease markers are located or to prevent treatment in a particular area with darker pigmentation, such as from scar tissue. In this case, the camera 36 may be fitted with an iris aperture 72 configured to selectively widen or narrow the opening through which the light is directed into the eye 38 of the patient. FIG. 19 illustrates an opening 74 on a camera 36 fitted with such an iris aperture 72. Alternatively, the iris aperture 72 may be replaced or supplemented by a liquid crystal display (LCD) 76. The LCD 76 acts as a dynamic aperture by allowing each pixel in the display to either transmit or block the light passing through it. Such an LCD 76 is depicted in FIG. 20.

Preferably, any one of the inventive systems 30, 30', 30" includes a display on a user interface with a live image of the retina as seen through the camera 36. The user interface may include an overlay of this live image of the retina to select areas where the treatment light will be limited or excluded by the iris aperture 72 and/or the LCD 76. The user may draw an outline on the live image as on a touch screen and then select for either the inside or the outside of that outline to have limited or excluded coverage.

By way of example, if the user identifies scar tissue on the retina that should be excluded from treatment, the user would draw an outline around the scar tissue and then mark the interior of that outline for exclusion from the laser treatment. The control system and user interface would then send the proper control signal to the LCD 76 to block the projected treatment light through the pixels over the selected scar tissue. The LCD 76 provides an added benefit of being useful for attenuating regions of the projected pattern. This feature may be used to limit the peak power output of certain spots within the pattern. Limiting the peak power of certain spots in the pattern with the highest power output can be used to make the treatment power more uniform across the retina.

Alternatively, the surgeon may use the fundus monitor to outline an area of the retina to be treated or avoided; and the designated area then treated or avoided by software directing the treatment beams to treat or avoid said areas without need or use of an obstructing LCD 76 diaphragm.

Although the present invention is particularly suited for treatment of retinal diseases, such as diabetic retinopathy and macular edema, it is contemplated that it could be used for other diseases as well. The system and process of the present invention could target the trabecular mesh work as treatment for glaucoma, accomplished by another customized treatment field template. It is contemplated by the present invention that the system and concepts of the present invention be applied to phototherapy treatment of other tissues, such as, but not limited to, the gastrointestinal or respiratory mucosa, delivered endoscopically, for other purposes.

In addition, the results or images from other retinal diagnostic modalities, such as OCT, retinal angiography, or autofluoresence photography, might be displayed in parallel or by superimposition on the display image of the patient's fundus to guide, aid or otherwise facilitate the treatment. This parallel or superimposition of images can facilitate identification of disease, injury or scar tissue on the retina.

Although several embodiments have been described in detail for purposes of illustration, various modifications may be made without departing from the scope and spirit of the invention. Accordingly, the invention is not to be limited, except as by the appended claims.

What is claimed is:

1. A system for performing retinal photostimulation, comprising:
   means for generating a plurality of pulsed laser light treatment beams having parameters selected so as to provide true subthreshold photocoagulation to applied retinal tissue;
   a coaxial wide-field non-contact digital optical viewing camera simultaneously projecting the laser light treatment beams to an area of a desired site of a retina for performing true subthreshold photocoagulation; and
   a mechanism that controllably moves the laser light treatment beams during pulse intervals from a first treatment area of the retina to at least one other treatment area of the desired site of the retina, and subsequently returns the laser light treatment beams to the previously treated first treatment area within a predetermined period of time during the same treatment session to simultaneously reapply the laser light treatment beams to that first treatment area.

2. The system of claim 1, wherein the mechanism is configured to controllably move the laser light treatment beams to achieve complete coverage of the retina.

3. The system of claim 1, wherein the mechanism controllably moves the laser light treatment beams to disease markers on the desired site.

4. The system of claim 1, wherein the generating means comprises a laser console and an optical mask that produces the plurality of treatment beams from a pulsed laser light treatment beam emitted from the laser console.

5. The system of claim 4, wherein the optical mask comprises
   diffractive optics.

6. The system of claim 1, further comprising a fundus image of the desired site for performing retinal true subthreshold photocoagulation displayed parallel to or superimposed over a result image from a retinal diagnostic modality.

7. The system of claim 1, wherein the mechanism is configured to controllably return the laser light treatment beams to the previously treated first treatment within less than a second from the previous application of the laser light treatment beams to the first treatment area.

8. The system of claim 7, wherein the laser light treatment beams are returned to the previously treated first treatment area by the mechanism within 1 millisecond to 3 milliseconds.

9. The system of claim 1, wherein the generating means comprises a plurality of laser consoles that generate a plurality of pulsed light treatment beams having a wavelength between 532 nm and 1300 nm, at least a plurality of the light treatment beams having different wavelengths.

10. The system of claim 9, wherein each of the treatment laser light beams has a wavelength between 750 nm and 1300 nm.

11. The system of claim 1, wherein the mechanism returns the plurality of laser light treatment beams to each treatment area until each treatment area is treated with 75 to 150 applications of treatment laser light.

12. The system of claim 1, wherein the mechanism is configured to controllably move the laser light treatment beams between single pulses of the treatment laser light treatment beams.

13. The system of claim 12, wherein the treatment laser light beams have an application pulse of less than a millisecond in duration.

14. The system of claim 13, wherein the treatment laser light pulse is 50 microseconds to 100 microseconds in duration.

15. The system of claim 1, wherein each of the plurality of treatment laser light beams has a wavelength greater than 532 nm.

16. The system of claim 15, wherein each of the treatment laser light beams have a wavelength between 750 nm-1300 nm.

17. The system of claim 1, wherein the treatment laser light beams each have a duty cycle of less than 10%.

18. The system of claim 17, wherein each of the treatment laser light beams has a duty cycle of 5% or less.

19. The system of claim 1, wherein the optical viewing system projects the light treatment beams such that adjacent treatment areas of the retina are separated by a distance of at least a 0.5 width of an immediately previously treated area to avoid thermal tissue damage.

20. The system of claim 1, wherein the viewing system projects
treatment light beams defining spaced apart spots having a diameter between 25 and 300 microns.

21. The system of claim 1, wherein the system is configured to generate and project the treatment light beams to a retinal irradiance of 100-590 Watts per square centimeter and raise the temperature of the retinal tissue between seven and fourteen degrees Celsius at least during application of the treatment light beams to the retinal tissue.

22. A system for performing retinal photostimulation, comprising:
a laser console generating a pulsed laser light treatment beam having parameters selected so as to provide true subthreshold photocoagulation to applied retinal tissue, including a wavelength between 532 nm and 1300 nm and a duty cycle of 10% or less;
an optical mask that the laser light treatment beam passes through to optically shape the laser light treatment beam into a plurality of laser light treatment beams;
a coaxial wide-field non-contact digital optical viewing camera simultaneously projecting the laser light treatment beams to an area of a desired site for performing retinal true subthreshold photocoagulation; and
a mechanism that controllably moves the laser light treatment beams during pulse intervals from a first treatment area of the retina to at least one other treatment area of the desired site of the retina spaced apart from the first treatment area a predetermined distance and avoiding thermal damage, and subsequently returns the laser light treatment beams to the previously treated first treatment area within a predetermined period of time comprising less than one second from the application of the laser light treatment beams to the first treatment area to reapply the laser light treatment beams to that first treatment area.

23. The system of claim 22, wherein the laser light treatment beams are controllably moved to achieve complete coverage of the retina.

24. The system of claim 22, further comprising a fundus image of the desired site for performing retinal true subthreshold photocoagulation displayed parallel to or superimposed over a result image from a retinal diagnostic modality.

25. The system of claim 22, wherein the mechanism returns the laser light treatment beams to each treatment area until each treatment area is treated with 75 to 150 applications of treatment laser light.

26. The system of claim 22, wherein the mechanism controllably moves the laser light treatment beams between single pulses of the treatment laser light beams.

27. A system for performing retinal photostimulation, comprising:
A plurality of laser consoles generating a plurality of pulsed laser light treatment beams having parameters selected so as to produce true subthreshold photocoagulation in applied retinal tissue, including each having a wavelength between 532 nm and 1300 nm and a duty cycle of 10% or less, and at least a plurality of the laser light treatment beams having a different wavelength;
a coaxial wide-field non-contact digital optical viewing camera simultaneously projecting the plurality of laser light treatment beams to an area of a desired site for performing retinal true subthreshold photocoagulation; and
a mechanism that controllably moves the plurality of laser light treatment beams during pulse intervals from a first treatment area of the retina to at least one other treatment area of the desired site of the retina spaced apart a predetermined distance from the first treatment area and avoiding thermal damage, and subsequently returns the plurality of laser light treatment beams to the previously treated first treatment area within a predetermined period of time comprising less than one second from the application of the laser light treatment beams to the first treatment area to reapply the laser light treatment beams to that first treatment area.

28. The system of claim 27, wherein the mechanism is configured to controllably move the laser light treatment beams until the entire retina is treated.

29. The system of claim 27, further comprising a fundus image of the desired site for performing retinal true subthreshold photocoagulation displayed parallel to or superimposed over a result image from a retinal diagnostic modality.

30. The system of claim 27, wherein the laser light treatment beams are controllably returned to the previously treated first treatment area by the mechanism within between 0.1 and 0.3 seconds from the previous application of the laser light treatment beams to the first treatment area.

31. The system of claim 27, wherein the mechanism returns the laser light treatment beams to each treatment area until each treatment area is treated with 75 to 150 applications of the treatment laser light beams.

32. The system of claim 27, wherein the mechanism controllably moves the laser light treatment beams between single pulses of the treatment laser light beams.

33. The system of claim 27, wherein each of the treatment laser light beams has a wavelength between 750 nm and 1300 nm.

* * * * *